US012589374B2

(12) United States Patent
Bough et al.

(10) Patent No.: US 12,589,374 B2
(45) Date of Patent: Mar. 31, 2026

(54) METHOD FOR MAKING MULTIPARTICULATES FROM A LIQUID FEED EMPLOYING A SPINNING DISC SPRAYER

(71) Applicant: Capsugel Belgium NV, Bornem (BE)

(72) Inventors: Joshua P. Bough, Cambridge (GB); Jan Bouquet, Bornem (BE); Nigel D. Harrison, Cambridge (GB); Cody A. Prather, Bend, OR (US); Gunther Van Goolen, Bornem (BE); Stefaan Jaak Vanquickenborne, Bornem (BE); Bart Verwilghen, Bornem (BE)

(73) Assignee: Lonza Sales AG (CH)

( * ) Notice: Subject to any disclaimer, the term of this patent is extended or adjusted under 35 U.S.C. 154(b) by 496 days.

(21) Appl. No.: 18/010,981

(22) PCT Filed: Jun. 15, 2021

(86) PCT No.: PCT/IB2021/055276
§ 371 (c)(1),
(2) Date: Dec. 16, 2022

(87) PCT Pub. No.: WO2021/255645
PCT Pub. Date: Dec. 23, 2021

(65) Prior Publication Data
US 2023/0226508 A1     Jul. 20, 2023

Related U.S. Application Data

(60) Provisional application No. 63/041,024, filed on Jun. 18, 2020.

(51) Int. Cl.
*B01J 2/02*     (2006.01)
*B05B 3/10*     (2006.01)
*A61K 9/16*     (2006.01)

(52) U.S. Cl.
CPC .............. *B01J 2/02* (2013.01); *B05B 3/1007* (2013.01); *B05B 3/1064* (2013.01); *A61K 9/1682* (2013.01)

(58) Field of Classification Search
CPC ....... B05B 3/10; B05B 3/1007; B05B 3/1014; B05B 3/1021; B05B 3/1028;
(Continued)

(56) References Cited

U.S. PATENT DOCUMENTS 1,506,226 A     8/1924   Dick
4,540,124 A *   9/1985   Haruch ................. B05B 3/1064
                                                        239/223
(Continued)

FOREIGN PATENT DOCUMENTS

EP     1689368 A1     8/2006
EP     1737433 B1     11/2007
(Continued)

OTHER PUBLICATIONS

International Search Report and Written Opinion, mailed Sep. 20, 2021, issued for International Patent Application No. PCT/IB2021/055276, 9 pages.
(Continued)

*Primary Examiner* — Andrew L Swanson
(74) *Attorney, Agent, or Firm* — Klarquist Sparkman, LLP

(57) ABSTRACT

A process for making multiparticulates, comprising providing a molten feed comprising an active ingredient and an excipient, and providing a spinning disc sprayer comprising a rotating disc having a feed-receiving surface driven from above by a hollow drive shaft, wherein axes of rotation of the hollow drive shaft and rotatable disc are coaxial and a downward end of the hollow drive shaft is disposed with a distributor for regulating flow of the molten feed into the
(Continued)

well, the distributor and the well together configured for providing a substantially radial, uniform outward flow of the molten feed across the feed-receiving surface.

17 Claims, 16 Drawing Sheets

(58) Field of Classification Search
CPC ... B05B 3/1035; B05B 3/1042; B05B 3/1057; B05B 3/1064; B05B 3/1071; B05B 3/1078; B05B 3/1085; B01F 25/74; B01F 25/741; B01F 25/742; B01J 2/02; B01J 2/06; B01J 2/08; B01J 2/14
See application file for complete search history.

(56) References Cited

U.S. PATENT DOCUMENTS

| | | | |
|---|---|---|---|
| 4,675,140 A | 6/1987 | Sparks et al. | |
| 7,625,507 B2 | 12/2009 | Ray et al. | |
| 7,736,672 B2 | 6/2010 | Ray et al. | |
| 7,887,844 B2 | 2/2011 | Appel et al. | |
| 7,951,403 B2 | 5/2011 | Friesen et al. | |
| 8,236,349 B2 | 8/2012 | Appel et al. | |
| 11,510,877 B2 | 11/2022 | Craig et al. | |
| 2005/0158220 A1* | 7/2005 | Ramshaw | B01J 19/128 |
| | | | 422/186 |
| 2005/0181061 A1* | 8/2005 | Ray | A61P 31/04 |
| | | | 424/489 |
| 2007/0116650 A1 | 5/2007 | Demirbuker | |
| 2010/0068276 A1 | 3/2010 | Friesen et al. | |
| 2011/0114745 A1* | 5/2011 | Buisson | B01J 2/04 |
| | | | 239/4 |
| 2014/0087169 A1* | 3/2014 | Koslow | B01F 23/45 |
| | | | 526/335 |
| 2016/0348222 A1* | 12/2016 | Isaac | C22C 38/22 |
| 2017/0239632 A1 | 8/2017 | Ito et al. | |
| 2017/0354599 A1* | 12/2017 | Diorio | A61K 31/122 |
| 2020/0323779 A1* | 10/2020 | Craig | A61K 9/1611 |

FOREIGN PATENT DOCUMENTS

| | | | |
|---|---|---|---|
| EP | 1691787 B1 | 7/2008 | |
| EP | 2091519 B1 | 6/2015 | |
| FR | 40 477 E 1 | 7/1932 | |
| JP | 2012-520176 A | 9/2012 | |
| JP | 2016155055 A | 9/2016 | |
| SU | 661 222 A1 | 5/1979 | |
| WO | WO 2012/028291 A1 | 3/2012 | |
| WO | WO 2016/031692 A1 | 3/2016 | |

OTHER PUBLICATIONS

Sescu, "Experimental and computational study on liquid atomization by slinger injector," PhD diss., University of Toledo, 2011.

* cited by examiner

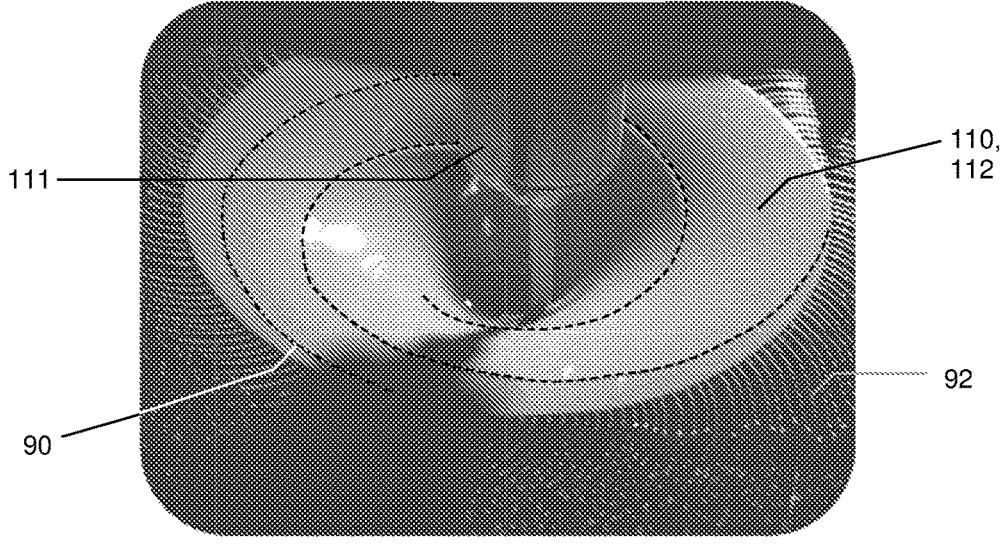
FIG. 2A
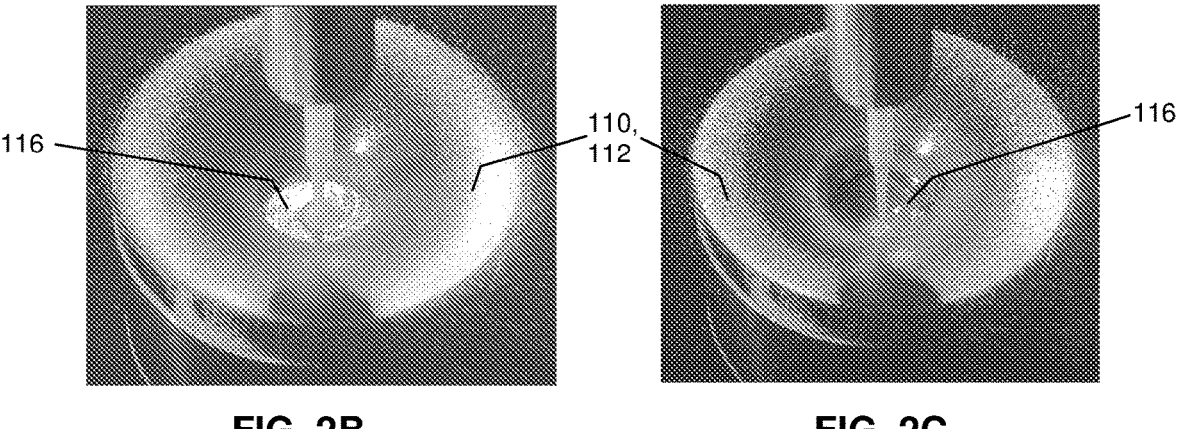
FIG. 2B                    FIG. 2C

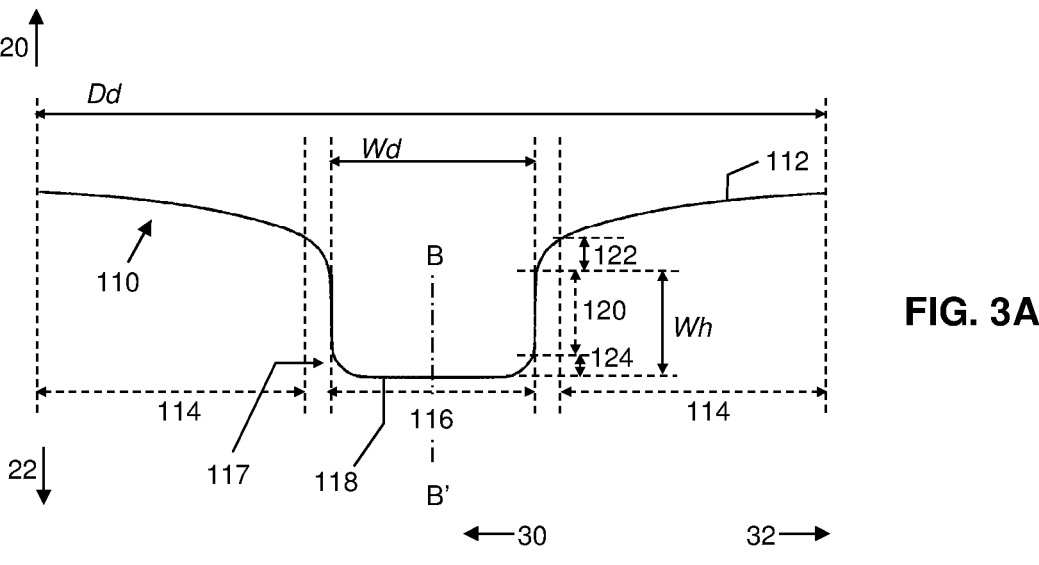
FIG. 3A
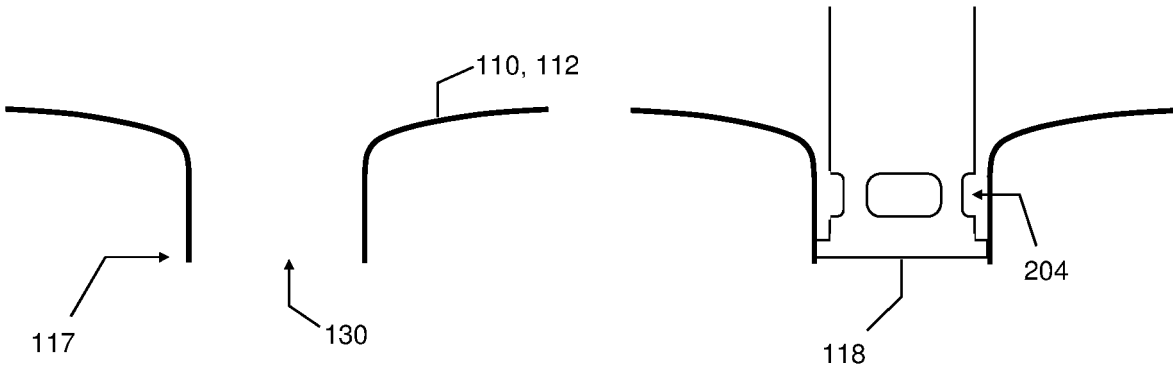
FIG. 3B
FIG. 3C
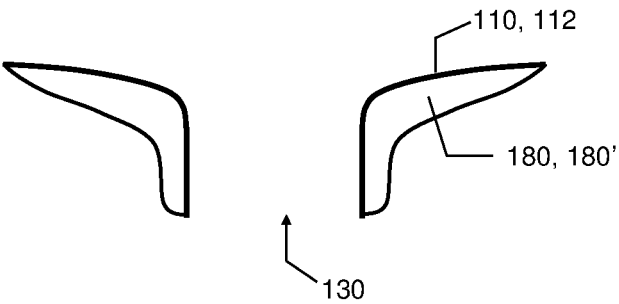
FIG. 3D

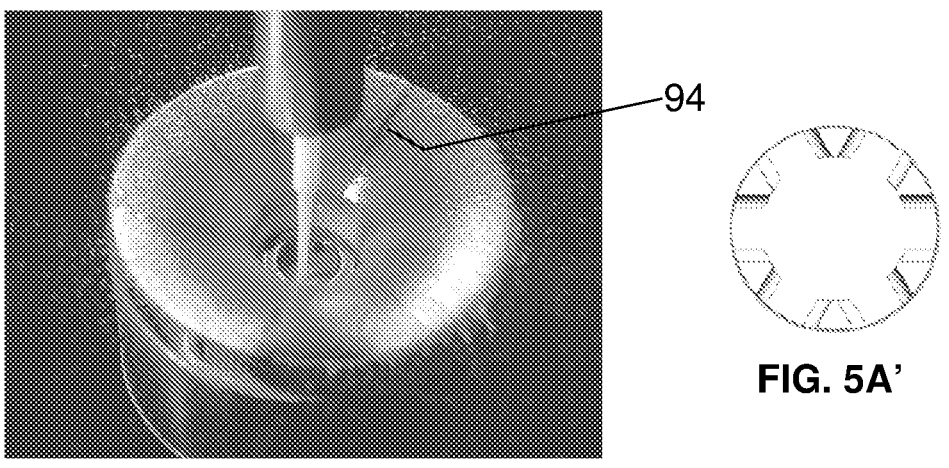
94
FIG. 5A'
FIG. 5A
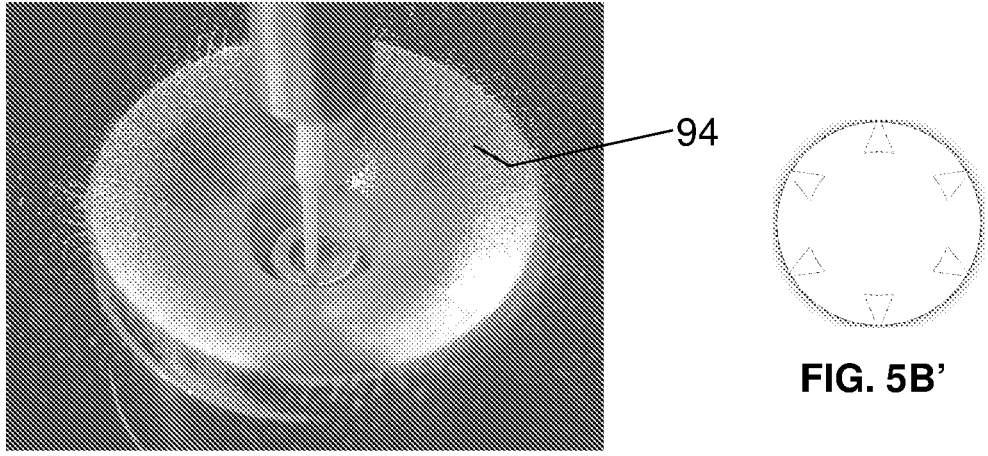
94
FIG. 5B'
FIG. 5B
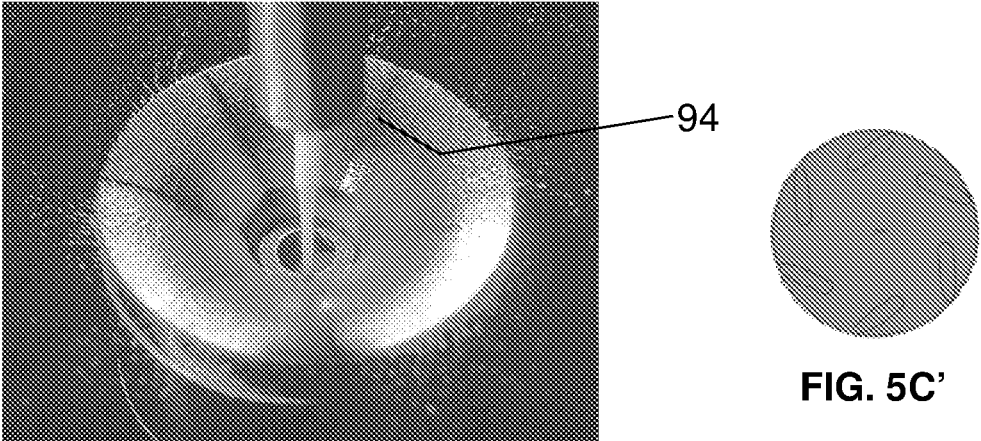
94
FIG. 5C'
FIG. 5C

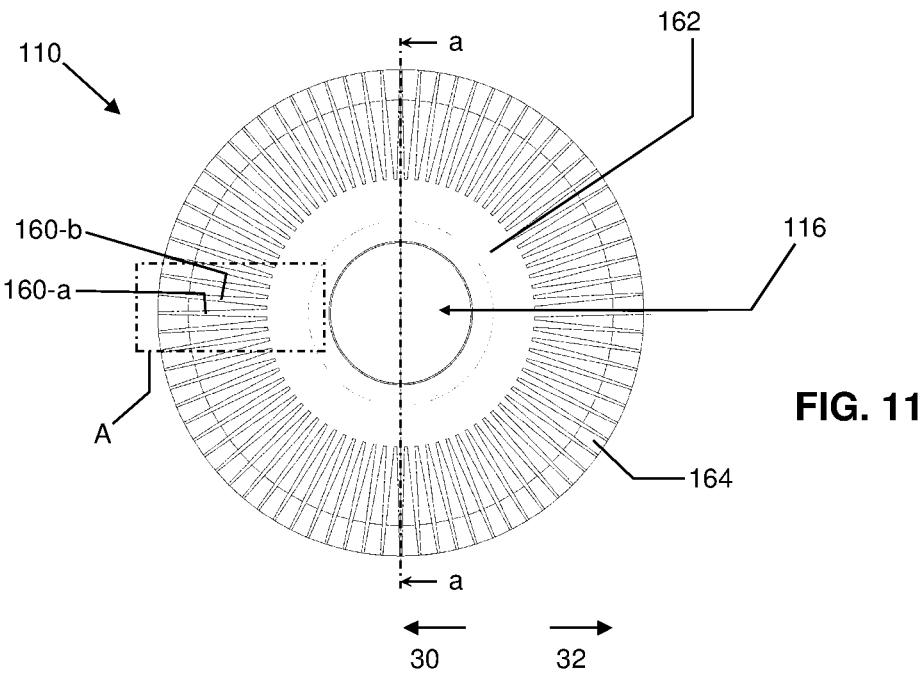
FIG. 11
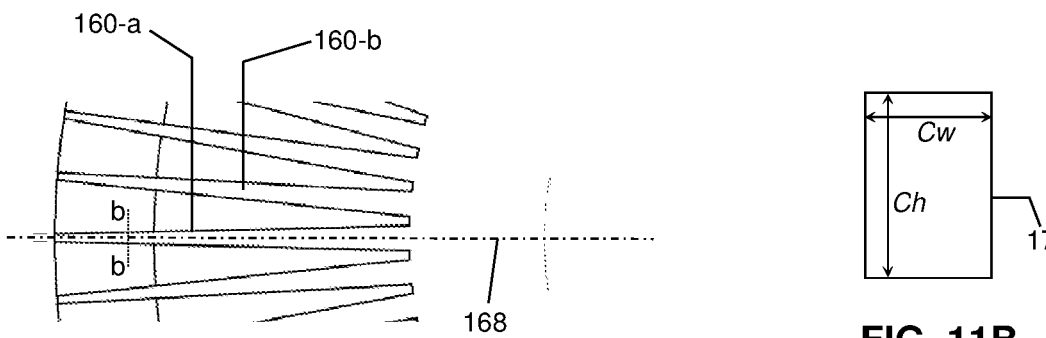
FIG. 11A
FIG. 11B
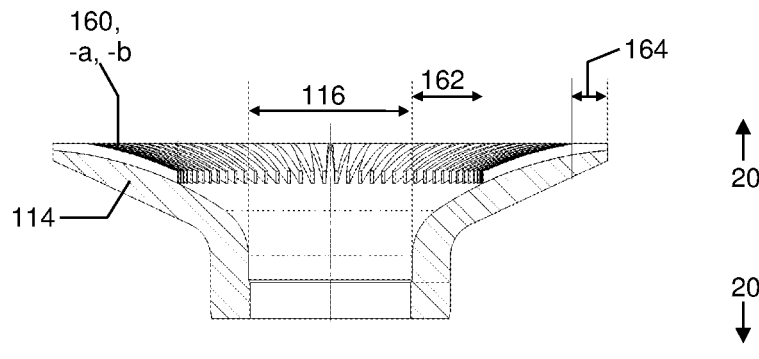
FIG. 12

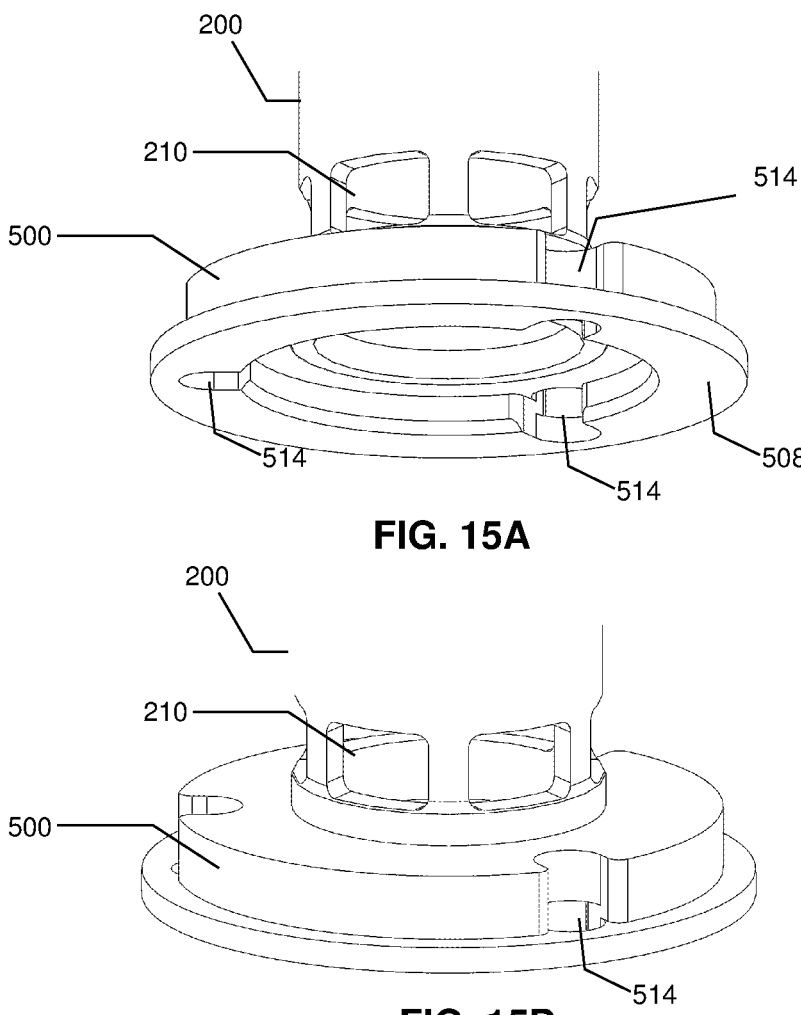
FIG. 15A
FIG. 15B
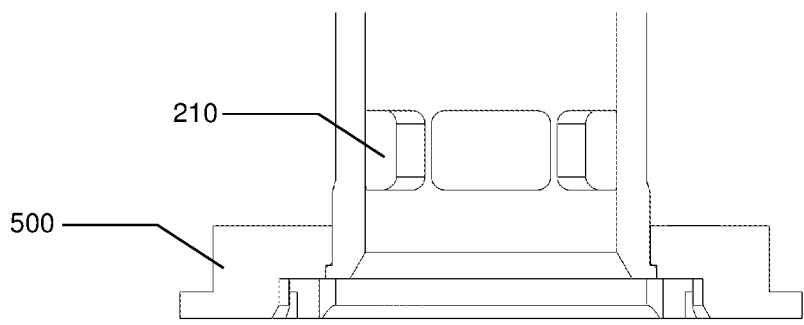
FIG. 15C

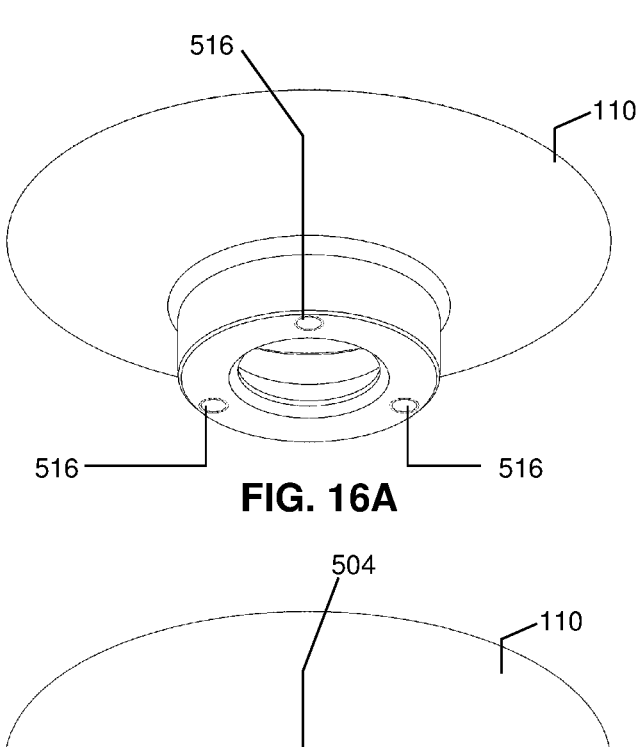
FIG. 16A
FIG. 16B
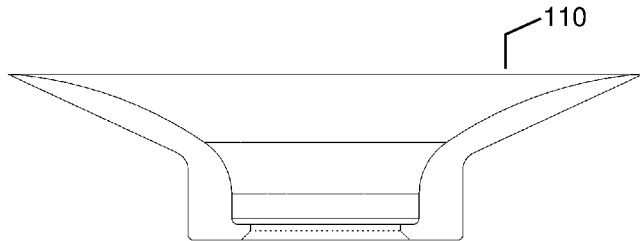
FIG. 16C

METHOD FOR MAKING MULTIPARTICULATES FROM A LIQUID FEED EMPLOYING A SPINNING DISC SPRAYER

CROSS REFERENCE TO RELATED APPLICATIONS

This is the U.S. National Stage of International Application No. PCT/IB2021/055276, filed Jun. 15, 2021, which was published in English under PCT Article 21(2), which in turn claims the benefit of U.S. Provisional Application No. 63/041,024, filed Jun. 18, 2020. The provisional application is incorporated herein in its entirety.

FIELD

The devices and methods described herein are in the field of spinning disc sprayer, also known as spinning disc atomiser. In particular, they relate to a spinning disc sprayer applied to preparation of multiparticulates from a molten feed, for instance in a melt-spray-congeal (MSC) process.

BACKGROUND

A typical spinning disc sprayer receives product feed onto a surface spinning disc, and centrifugal forces expels the feed radially outward where it leaves the surface as small particles. Spinning disc sprayers have been used to make particles in solvent based spray drying. One such device, for example, is described in WO 2016/087261.

In many applications particle size must be within defined ranges. In melt-spray-congeal (MSC) processes, for instance, the spinning disc of a rotary atomiser is placed at the top of a large process container and molten feed is fed onto the spinning disc that expels particles that congeal mid-air in the container and fall towards the base where they are collected as solid particles. The MSC process may be used to produce lipid multiparticulates for delivery of drugs, and control of particle size is critical obtaining a uniform produce containing a consistent quantity of drug.

It is an aim herein to provide a method and a spinning disc sprayer for producing particles having a narrower particle size distribution.

SUMMARY

Disclosed herein are various embodiments directed to spinning disc sprayers for preparing multiparticulates from a molten feed, and method of forming multiparticulates using the same.

Provided herein is a process for making multiparticulates, comprising providing a molten feed comprising an active ingredient and an excipient and providing a spinning disc sprayer (100) comprising: a rotating disc (110) having a feed-receiving surface (112) and an axis of rotation (B-B'), and a drive hollow shaft (200) having a longitudinal shaft lumen (202) and an axis of rotation (A-A') attached to the rotating disc (110). The feed-receiving surface can define a well (116) centered on the axis of rotation (B-B').

The molten feed can be directed through the lumen (202) onto the feed-receiving surface (112), and atomizing the molten feed from the rotating disc (110) to form solid multiparticulates. The axes of rotation of the hollow drive shaft (A-A') and rotatable disc (B-B') can be coaxial and a downward end (22) of the hollow drive shaft (200) can be disposed with a distributor (204) for regulating flow of the molten feed into the well (116). The distributor (204) and the well (116) can be configured together for providing a substantially radial, uniform outward flow of the molten feed across the feed-receiving surface (112).

In some embodiments, the feed-receiving surface (112) may comprise a peripheral flared portion (114) that slopes gradually in a central (30) and downwards (22) direction towards the well (116), and the well (116) extends further downwards (22) towards a well base end (117). At least a portion of the feed-receiving surface of the well (116) can be more steep than at least a portion of the feed-receiving surface of the flared portion (114).

In other embodiments, the flared portion (114) of the feed-receiving surface (112) may be provided with a plurality of radial channels (160, -a, -b), wherein each channel is a conduit for molten feed, open at an upwards (20) side, and open at both peripheral (32) and central (30) ends and configured to conduct molten feed from the well (116) to the peripheral edge of the flared portion (114).

In still other embodiments, the rotatable disc (110) may be disposed on a downward side (22) with a heat generator (180) configured to regulate a temperature of the feed-receiving surface. In some embodiments, the number of rotatable discs (110) and feed-receiving surfaces (112) can be one.

In some embodiments, the distributor (204) can comprises a plurality of apertures (210) disposed around a circumference of the downward end (22) of the hollow drive shaft (200) for the outflow of the molten feed. In some embodiments, a pillar (212, a, b) may be disposed between adjacent aperture pairs (210, a, b), the pillar (212, a, b) having in transverse cross section a pillar outer edge (214, a), two pillar side edges (216, a, b; 218, a, b) and optionally a pillar inner edge (220, a), wherein the side edges (216, b and 218b) of the pillar (212, b) converge in a direction towards the center (30) of the hollow drive shaft (200).

The hollow drive shaft and is dismountably attachable at its downward end (22) through an opening (130) in the well base end (117) of the rotatable disc (110). The hollow drive shaft (200) can be dismountably attachable at the upward end (20) to a releasable mounting (350). The spinning disc sprayer (100) can be further provided with a hollow outer support shaft (270) having a longitudinal shaft lumen (272) for receiving the drive shaft (200). The spinning disc sprayer (100) can be further provided with an optical camera, configured to capture during spraying one or more images of at least a part of the feed-receiving surface, and feed-particles being sprayed from the feed-receiving surface (112).

In some embodiments, the spinning disc sprayer (100) may be configured for partial insertion into a process container (400) having a container volume (404) in which particles ejected from the rotatable disc (110) can undergo transformation, wherein the rotatable disc (110) is immersed in the container volume and the upward end of the spinning disc sprayer is outside the container. The liquid feed may be a molten feed comprising at least one active agent and at least one excipient, optionally wherein the at least one excipient is an alkyl-containing glycerol such as a mixture of mono-, di- and triglyceryl behenates (Compritol 888), glyceryl tristearate (Dynasan 118), hydrogenated cottonseed oil (Lubritab), hydrogenated castor oil (Kolliwax HCO), stearyl alcohol (Kolliwax SA), stearic acid and palmitic acid 50 (Kolliwax S), carnauba wax, candelilla wax, stearoyl polyoxylglyceride (Gelucire 50/13), or polyglycerol esters of fatty acids. The molten feed may further comprise at least one of a pore former, a swelling agent, a modified release material, and a viscosity modifier. The multiparticulates may have a particle size range of from 100 μm and up to about 3 mm.

Additional features and implementations of the disclosed spinning disc sprayers for preparing multiparticulates from a molten feed, and methods of forming multiparticulates using the same are provided herein. The foregoing and other objects, features, and advantages of the invention will become more apparent from the following detailed description, which proceeds with reference to the accompanying figures.

BRIEF DESCRIPTION OF THE DRAWINGS

FIGS. 2A to 2C are photographs of results of different tests of spinning disc sprayer (100); FIG. 2A—axis of rotation of the rotatable disc (110) and feed outlet (111) supplying liquid feed (molten feed) are eccentric; FIG. 2B—well (116) is provided with a flat well floor receiving liquid feed (suspension); FIG. 2C—well (116) is provided with a concave well floor receiving liquid feed (suspension);

FIGS. 3A to 3C are various cross-sectional views of the rotatable disc (110);

FIG. 3D is a cross section of the rotatable disc (110) showing heat emitter;

FIGS. 5A to 5C are photographs of results of different tests of spinning disc sprayer (100); FIG. 5A—flow pattern using pillars having side edges converging towards a centre of the of the hollow drive shaft (200) (FIG. 5A'); FIG. 5B—flow pattern using pillars having side edges converging towards a periphery of the of the hollow drive shaft (200) (FIG. 5B'); FIG. 5C—flow pattern using non-symmetrical pillars (FIG. 5C');

FIG. 6A longitudinal cross-section through hollow drive shaft and rotatable disc; FIG. 6B isometric view of hollow drive shaft bayonet fitting; FIG. 6C isometric view of rotatable disc bayonet fitting; FIG. 6D isometric view of shaft plug that engages with hollow drive shaft and rotatable disc;

FIG. 7A longitudinal cross-section through shaft plug; FIG. 7B longitudinal cross-section through shaft plug clamping bayonet fitting together; FIG. 7C longitudinal cross-section through shaft plug provided with key;

FIG. 8A mixed isometric/transparent view of arrangement of shafts and tubes within the spinning disc sprayer (100); transverse cross-sectional view of arrangement of shafts and tubes within the spinning disc sprayer (100) with respect to chassis assembly—rotating parts represented by broken lines, parts stationary to chassis represented by solid lines;

FIGS. 11, 11A and 11B are schematic illustrations of a rotatable disc provided with radial channels; FIG. 11A is enlargement of FIG. 11 box A; FIG. 11B is cross-section along FIG. 11A b-b; and FIG. 12 is a cross-sectional view of rotatable disc of FIG. 11 along plane a-a.

FIGS. 15A to 15C are views of a flange of a hollow drive member.

FIGS. 16A to 16C are views of a rotatable disc member configured to be attached to a flange of a hollow drive shaft.

DETAILED DESCRIPTION

Figure 1:
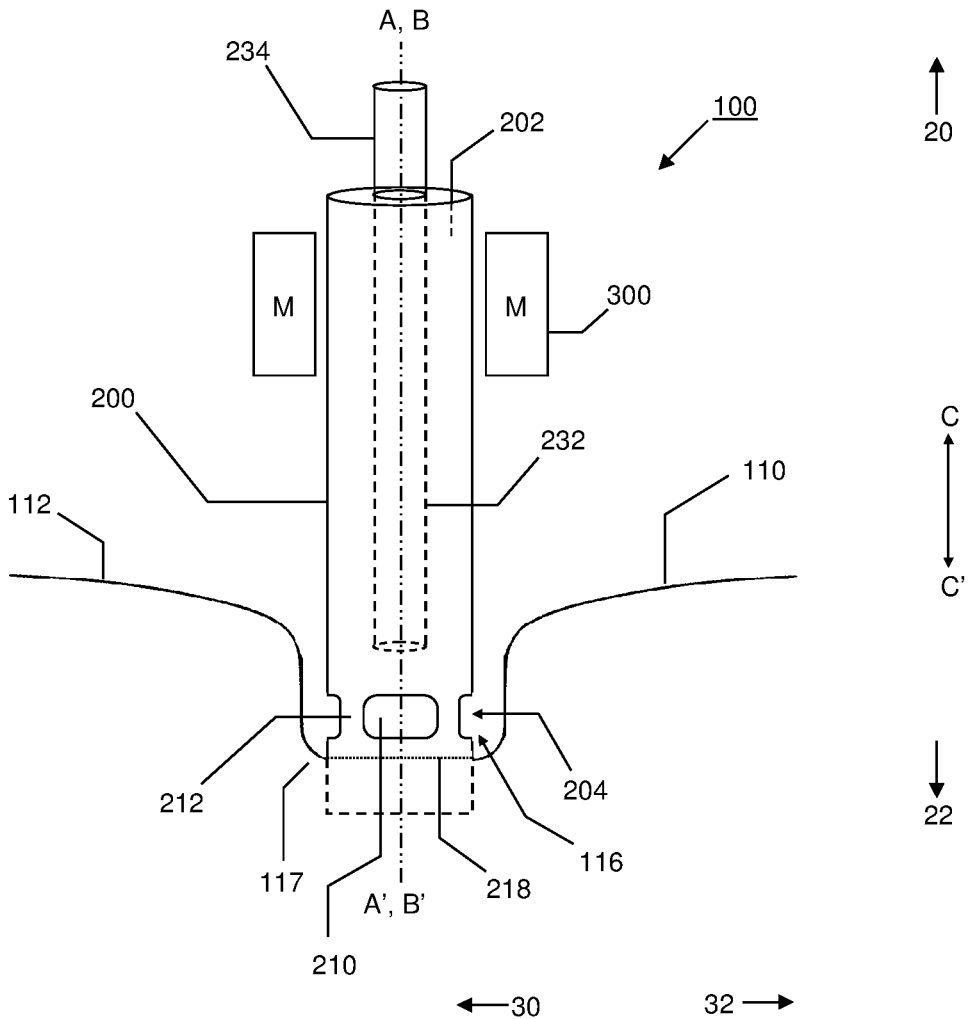
FIG. 1 is a schematic diagram of the spinning disc sprayer (100) as described herein.

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed embodiments. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of the members, or to any two or more of the members, such as, e.g., any ≥3, ≥4, ≥5, ≥6 or ≥7 etc. of the members, and up to all the members.

All references cited in the present specification are hereby incorporated by reference in their entirety. In particular, the teachings of all references herein specifically referred to are incorporated by reference.

Unless otherwise defined, all terms used in this disclosure, including technical and scientific terms, have the meaning as commonly understood by one of ordinary skill in the art to which the technology of this disclosure belongs. By means of further guidance, term definitions are included to better appreciate the teaching of the present disclosure.

In the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present disclosure, reference is made to the accompanying drawings that form a part hereof, and in which are shown by way of illustration only of specific embodiments in which the disclosed subject matter may be practiced. Parenthesized or emboldened reference numerals affixed to respective elements merely exemplify the elements by way of example, with which it is not intended to limit the respective elements. It is to be understood that other embodiments may be utilized, and structural or logical changes may be made without departing from the scope of the present invention. The following detailed description, therefore, is not to be taken in a limiting sense, and the scope of the present invention is defined by the appended claims.

The terms "upward" (20) and "downward" (22) are used here to refer to opposing ends or sides of spinning disc sprayer or parts thereof, wherein the feed to be sprayed flows from a feed inlet from an upwards direction towards a downward direction. Upwards is typically towards a top end of the spinning disc sprayer or a part thereof, and downward is towards a base end of the spinning disc sprayer or a part thereof. A transverse cross-section refers to a section across a plane perpendicular to an axis e.g. axis of rotation (A-A', B-B').

The terms "central" (30) is used here to refer to a lateral or sideways direction towards central axis of rotation (A'A') of the hollow drive shaft (200) axis, and "peripheral" (32) is used here to refer to a lateral or sideways direction away from the central axis of rotation (A'A') of the hollow drive shaft (200) axis. See, for example, FIG. 1.

Provided herein is a method and spinning disc sprayer (100) for producing multi-particulates from a liquid feed, in particular from a molten feed. The spinning disc sprayer (100) atomises the liquid feed, producing the multiparticulates. An exemplary spinning disc sprayer (100) is shown in FIG. 1.

Provided herein are methods for making multiparticulates by applying a liquid feed to a spinning disc sprayer (100). An exemplary method comprises the steps:

providing a liquid feed;
  providing a spinning disc sprayer (100) as described
    herein comprising:

a rotating disc (110) having a feed-receiving surface (112) and an axis of rotation (B-B'), the feed-receiving surface defining a well centered on the axis of rotation (B-B'); and a drive shaft (200) having a longitudinal shaft lumen (202) and an axis of rotation (A-A') attached to the rotating disc (110);

directing the liquid feed through the lumen (202) onto the feed-receiving surface (112), and atomizing the liquid feed from the rotating disc (110) to form solid multi-particulates.

Also provided herein are spinning disc sprayers (100) for producing multi-particulates from a liquid feed. An exemplary spinning disc sprayer (100) comprises a rotating disc (110) having a feed-receiving surface (112) and an axis of rotation (B-B'). The feed-receiving surface (112) defines a well (116) centered on the axis of rotation (B-B'). The spinning disc sprayer (100) further comprises a drive shaft (200) having a longitudinal shaft lumen (202) and an axis of rotation (A-A') attached to the rotating disc (110). The liquid feed is directed through the lumen (202) onto the feed-receiving surface (112), and liquid feed is atomised by the rotating disc (110) to form solid multiparticulates. The axes of rotation of the hollow drive shaft (A-A') and rotatable disc (B-B') are coaxial.

A downward end (22) of the hollow drive shaft (200) is disposed with a distributor for regulating flow of the molten feed into the well, the distributor configured to regulate outward flow of the molten feed across the feed-receiving surface (112) in a substantially uniform manner. A downward end (22) of the hollow drive shaft (200) may disposed with a distributor for regulating flow of the molten feed into the well, the distributor (204) and the well (116) together configured for providing a substantially radial, uniform outward flow of the molten feed across the feed-receiving surface (112). The distributor may be further configured to regulate outward flow of the molten feed across the feed-receiving surface (112) in a substantially radial manner.

The spinning disc sprayer (100) has an upward (20) and downward (22) end. The spinning disc sprayer comprises the rotatable disc (110), having a feed-receiving surface (112) facing upward (20). A hollow drive shaft (200) having a longitudinal shaft lumen (202) is attached (dismountably or non-dismountably) to a centre of the rotatable disc (110).

Herein, the spinning disc sprayer (100) and part thereof such as the outer support shaft 270, hollow drive shaft (200), heating element tube (236), rigid feed tube (232) have an axial direction (C-C') that is parallel to the axis of rotation (A-A') of the hollow drive shaft (200).

The hollow drive shaft (200) extends upwards (20). A motor unit (300) is provided disposed upwards (20) of the rotatable disc (110) for application of torque to the drive shaft (200). The drive shaft (200) is dismountably connected to a torque output of the motor unit (300).

The downward end (22) of the hollow drive shaft (200) is disposed with the distributor (204) for regulating flow of the liquid onto the feed-receiving surface (112). The distributer (204) may comprise a plurality apertures (210) in connection with the drive shaft lumen (202) for outward flow of feed concentric with an axis of rotation of the rotatable disc (110) onto the feed-receiving surface (112).

By providing the hollow drive shaft (200) attached from above to the rotatable disc (110), and by providing the hollow drive shaft (200) lumen (202) with a distributer (204) for conveying feed directly onto the feed-receiving surface (112), the centre of the outlet of the feed, the axis of rotation (A-A') of the hollow drive shaft (200), and axis of rotation (B-B') of the rotatable disc (110) are co-axially aligned. By this alignment, feed is applied and propelled across the feed-receiving surface (112) in a more even manner, leading to a narrower size distribution of particles, in particular for high-throughput application.

Where the feed is not aligned with the axis of rotation (A-A') of the hollow drive shaft (200), and axis of rotation (B-B') of the rotatable disc (110) i.e. there is an eccentric feed, there is a local increase in film thickness that creates larger particles upon atomisation. FIG. 2A shows an example of an eccentric feed onto a feed-receiving surface (112) from a feed outlet (111) that is slightly off centre; it produces an uneven, spiral (90) of feed across the feed-receiving surface (112), resulting in droplets (92) of uneven size being expelled from the surface. Eccentric feed is apparent in many existing designs where a rotatable disc is driven from below, and feed is poured onto the disc surface from above by a disconnected feed outlet (111). Alignment of the feed outlet (111) and centre of rotation of the rotatable disc (110) is difficult, especially in melt-spray-congeal (MSC) processes; in such processes the rotatable disc (110) is positioned at the top of a large process container so that the droplets produced rain down and congeal mid-air in the container where they are collected as solid particles at the base. Because the rotatable disc (110) must be positioned at the top of the large process container, it is supported and driven from below by a long shaft (e.g. 2-3 m in length). The presence of the long shaft makes alignment of the rotatable disc (110) and the disconnected feed outlet (111) at the top of the large process container difficult.

The present configuration where drive shaft lumen (202) supplies feed to a centre of the feed-receiving surface (112) by attachment from above of the hollow drive shaft (200) to the rotatable disc (110) ensures that the feed is brought into concentric or co-axial alignment with the axes of rotation (A-A', B-B').

The liquid feed may be any that is atomizable. Preferably the liquid feed is a molten feed. The molten feed is typically employed in a spray congealing process for making multi-particulates. The molten feed may be a homogenous solution or suspension. The molten feed have a viscosity of 1-1000 cP, preferably ~40-400 cP.

The liquid feed, in particular the molten feed, may contain one or more active agents. The active agent is a component that exerts a desired physiological effect on an animal, preferably a mammal, including but not limited to humans. The "active" as referred to herein may be directed only to humans.

Non-limiting examples of active agents include but are not limited to drugs, supplements, dietary supplements, such as vitamins or provitamins A, B, C, D, E, PP and their esters, carotenoids, anti-radical substances, hydroxyacids, antiseptics, molecules acting on pigmentation or inflammation, biological extracts, antioxidants, cells and cell organelles, antibiotics, macrolides, antifungals, itraconazole, ketoconazole, antiparasitics, antimalarials, adsorbents, hormones and derivatives thereof, nicotine, antihistamines, steroid and non-steroid anti-inflammatories, ibuprofen, naproxen, cortisone and derivatives thereof, anti-allergy agents, antihistamines, analgesics, local anesthetics, antivirals, antibodies and molecules acting on the immune system, cytostatics and anticancer agents, hypolipidemics, vasodilators, vasoconstrictors, inhibitors of angiotensin-converting enzyme and phosphodiesterase, fenofibrate and derivatives thereof, statins, nitrate derivatives and anti-anginals, beta-blockers, calcium inhibitors, anti-diuretics and diuretics, bronchodilators, opiates and derivatives thereof, barbiturates, benzodiazepines, molecules acting on the central nervous system, nucleic acids, peptides, anthracenic compounds, paraffin oil, polyethylene glycol, mineral salts, antispasmodics, gastric anti-secretory agents, clay gastric dressings and polyvinylpyrrolidone, aluminum salts, calcium carbonates, magnesium carbonates, starch, derivatives of benzimidazole, and combinations of the foregoing.

Other non-limiting examples of active agents include dextromethorphan, fexofenadine, guaifenesin, loratadine, sildenafil, vardenafil, tadafil, Olanzapine, Risperdone, Famotidine, Loperamide, Zolmitriptan, Ondansetron, Cetirizine, Desloratadine, Rizatriptan, Piroxicam, Paracetamol, Phloro-glucinol, Nicergoline, Metopimazine, Dihydroergotamine, Mirtazapine, Clozapine, Zolmitriptan, Prednisolone, Levodopa, Carbidopa, Lamotrigine, Ibuprofen, Oxycodone, Diphenhydramine, Ramosetron, Tramadol, Zolpidem, Fluoxetine, Hyoscyamine, and combinations thereof.

The active agent is preferably crystalline (with a melting point higher than the excipient) but could be amorphous. It may be soluble or insoluble in excipients (preferably insoluble). It is typically homogenous when mixed with molten excipients. Preferably it has a particle size of less than 50 μm. It may be present in a quantity of 60% w/w of the multiparticulates.

The liquid feed, more in particular molten feed, may contain one or more excipients (also known as matrix material). The excipient binds at least the active agent and, where present, the pore former. The presence of excipient creates a smooth round sphere upon solidification of molten feed containing the active agent. The excipient may be solid at room temperature. The excipient may be liquid above room temperature. It may have a melting point at a temperature in a range of 45-95° C. Preferably it has a lower melting point than the active agent. It may rapidly congeal to form a solid. It may be present in a quantity of at least 30% w/w of the multiparticulates.

Non-limiting examples of excipient include one or more of:

highly purified forms of waxes such as carnauba wax, white and yellow beeswax, microcrystalline wax, candelilla wax, and paraffin wax;

long-chain alcohols such as stearyl alcohol, cetyl alcohol and polyethylene glycol polyethylene glycol;

poloxamers;

polyoxyethylene alkyl ethers;

long-chain fatty acid esters (also known as fats), such as glyceryl monooleate, glyceryl mono- and distearate, glyceryl palmitostearate, polyethoxylated castor oil derivatives, mixtures of mono-, di-, and trialkyl glycerides, including mixtures of glyceryl mono-, di-, and tribehenate, glyceryl tristearate, glyceryl tripalmitate and hydrogenated vegetable oils, including hydrogenated cottonseed oil and hydrogenated castor oil;

glycolized fatty acid esters, such as polyethylene glycol stearate and polyethylene glycol distearate;

short to medium chain fatty acid esters, such as isopropyl palmitate, isopropyl myristate, triethyl citrate, lecithin, triacetin, and dibutyl sebacate;

polysorbates;

carboxylic acids such as stearic acid, benzoic acid, citric acid, fumaric acid, lactic acid, maleic acid, palmitic acid, caprylic acid, capric acid, lauric acid, arachidic acid, behenic acid, and lignoceric acid;

polyoxylglycerides such as stearoyl polyoxylglyceride (Gelucire 50/13) and lauroyl polyoxylglyceride (Gelucire 44/14);

polyglycerol esters of fatty acids.

Especially preferred excipients are an alkyl-containing glycerol such as a mixture of mono-, di- and triglyceryl behenates (Compritol 888), glyceryl tristearate (Dynasan 118), hydrogenated cottonseed oil (Lubritab), hydrogenated castor oil (Kolliwax HCO), stearyl alcohol (Kolliwax SA), stearic acid and palmitic acid 50 (Kolliwax S), carnauba wax, candelilla wax, stearoyl polyoxylglyceride (Gelucire 50/13), polyglycerol esters of fatty acids.

Examples of excipients that are lipid matrix materials are known in the art, for instance in WO 2015/189726 or its equivalent e.g. US 2017/0112762, which is incorporated herein by reference. WO 2015/189726 describes at [0049] to [0065] instances of lipid matrix materials that may be suitable as an excipient in the formation of multiparticulates.

The liquid feed that is a molten feed may contain one or more pore formers (also known as dissolution enhancer). A pore former is a material with aqueous solubility that increases the rate of water uptake by the core by increasing the effective water permeability of the multiparticulates. It may, for instance, cause formation of pores or channels throughout the excipient material. The pore former may be solid at room temperature. The pore former may be liquid above room temperature. It may have a melting point at a temperature in a range of 45-95° C. Preferably it has a lower melting point than the active agent. It may have an aqueous solubility. It may increase water uptake in the core to enhance active agent dissolution. It may be present in a quantity of 5-30% w/w of the multiparticulates. Preferably, it is soluble in the excipient in the molten state and phase separated in the solid state.

Non-limiting examples of pore former include one or more of: poloxamers such as Kolliphor P188 and Kolliphor P407; alcohols such as stearyl alcohol, cetyl alcohol, and polyethylene glycol; povidone; docusate salts; polyglycerol esters of fatty acids; polyoxyethylene alkyl ethers; polyoxyethylene alkyl esters; alkyl polyglycol ethers; polyoxyethylene castor oil derivatives; polysorbates; sodium lauryl sulfate; sorbitan monoesters; mixtures of mono-, di- and tri-alkyl glycerides and mono- and di-fatty acid esters of polyethylene glycol; sugars such as glucose, xylitol, sorbitol and maltitol; salts such as sodium chloride, potassium chloride, lithium chloride, calcium chloride, magnesium chloride, sodium sulfate, potassium sulfate, sodium carbonate, magnesium sulfate and potassium phosphate; amino acids such as alanine and glycine; and mixtures thereof.

A preferred dissolution enhancer comprises a poloxamer (Kolliphor P407), polyglycerol esters of fatty acids, alkyl polyglycol ethers.

The liquid feed, in particular the molten feed, may contain one or more other components. Non-limiting examples of other components include:

One or more swelling agent to rupture core and facilitate immediate drug release. Non-limiting examples of swelling agents include: sodium starch glycolate, croscarmellose sodium, crospovidone;

One or more modified release materials to slow dissolution. Non-limiting examples of modified release materials include:

Dialkylphthalates such as dibutyl phthalate;

Hydrocarbon waxes such as carnauba wax, candelilla wax, beeswax, microcrystalline wax, and paraffin wax;

One or more viscosity modifiers for to change viscosity of the molten feed to make it more amenable to proper atomization.

Viscosity reducing excipients include for instance stearyl alcohol, cetyl alcohol, low molecular weight polyethylene glycol, isopropyl alcohol, water Viscosity increasing excipients for instance microcrystalline wax, paraffin wax, high molecular weight polyethylene glycol, poloxamer, ethyl cellulose, hydroxypropyl cellulose, hydroxypropyl methyl cellulose, methyl cellulose, silicon dioxide, microcrystalline cellulose, magnesium silicate, sugars, and salts.

The liquid feed that is a molten feed may comprise one or more of i) at least one active agent, ii) at least one excipient, iii) at least one pore former, and iv) at least one other component. Preferably, the liquid feed that is a molten feed comprises i), ii), optionally iii), and optionally iv). Preferably the liquid feed that is a molten feed comprises i), ii), iii), and optionally iv). Preferably the liquid feed comprises i), ii), iii), and iv). The liquid feed forms multiparticulates according to a method described herein.

Multiparticulates formed by a method of the present disclosure may comprise one or more active ingredients, an optional one or more pore formers, an optional one or more other ingredients, encapsulated in a continuous phase of one or more excipients; the aforementioned components are present in the molten feed described elsewhere herein. Multiparticulates may have a particle size smaller than 150 μm and up to about 3 mm. Multiparticulates may have a particle size and distribution according to the application. For pharmacological application, for instance, particle size range of from about 100 to about 500 μm. Particle size distribution span may be 0.6-0.9.

Subsequent solid multiparticulates may be coated. Non-limiting examples of coating include:

A cosmetic coating to provide a certain appearance;

A reverse enteric coating to delay release in the mouth providing taste-masking;

An enteric coating to protect the active agent from the acidic environment or delay the drug release in the stomach.

The number of rotatable discs (110) attached to the hollow drive shaft (200) may be only 1. The number of feed receiving surfaces (112) may be only 1. The rotatable discs (110) may be formed from a single piece. The feed receiving surface (112) may be formed from a single piece. The feed-receiving surface (112) comprises a peripheral (32) flared portion (114) that slopes gradually in a central (30) and downwards (22) direction towards a central well (116). An exemplary rotatable disc (110) is shown in FIGS. 3A to 3C.

The well (116) is configured to receive and hold feed, which is centrifuged out of the well (116) and along the peripheral flared portion (114). The well (116) has a cup shape approximately with an inner portion having substantially vertical walls, the vertical walls transitioning to an outward flared portion (114) of the disc (110). At least a portion (e.g. all or substantial portion) of the feed-receiving surface of the well (116) may be more steep than at least a portion (e.g. all or substantial portion) of the feed-receiving surface of the flared portion (114). The steepness of a surface is determined by its incline compared with the axis of rotation (B-B') of the rotatable disc; a steeper surface is more parallel to the axis of rotation (B-B'). The feed-receiving surface of the well (116) may comprises a side wall (120), all or a substantial portion of which is parallel to the axes of rotation (B-B') of the rotatable disc or inclined at an angle thereto of less than ±10 deg. More than 50%, preferably more than 75% of the height (Wh) of the well (116) may have a side wall that is parallel to the axis of rotation (B-B') of the rotatable disc (110)

The feed-receiving surface of the well (116) extends further downwards (22) towards a well base end (117). The feed-receiving surface of the well base end (117) is sealed-off so as to retain feed within the well (116). The well base end (117) may be sealed-off by a continuation of the surface of the well (116) in a central direction (30), or by another element such as the hollow drive shaft (200), or shaft plug (250) that co-operates with the rotatable disc (110).

By providing the rotatable disc (110) with a well (116) a vortex of feed is readily formed with the well (116) having a centre aligned with the axis of rotation (A-A') of the hollow drive shaft (200), and with axis of rotation (B-B') of the rotatable disc (110).

The inventors have found that the vortex created in the well (116) smooths-out uneven flow into the well (116), thereby spreading feed across the feed-receiving surface (112) in a more even manner, leading to a narrower size distribution of particles. The geometry of the well (116) aids in uniformly redistributing the molten feed from disturbances that may occur due to the hollow drive shaft lumen (202) or pillars (212). FIG. 2B (planar well floor) and FIG. 2C (concave well floor) each show a rotatable disc (110) having a well (116) exhibiting good performance (feed rate 10 Kg/hr, disc speed 3000 rpm) with a minimal of feed-starved area across the feed-receiving surface.

A well floor (118) is formed where the well base end (117) is sealed off. The well floor (118) may be circular. The well floor (118) may be planar. The well floor (118) may be concave. The well floor (118) may be formed by a continuation of the wall of the well (116) in a central (30) direction (e.g. FIG. 3A). The well floor (118) may be formed by a part of the hollow drive shaft (200) (e.g. FIG. 3C). The well floor (118) may be formed by a body (252) of a shaft plug (250). The well base end (117) may be provided with an opening (130) for dismountable attachment to the hollow drive shaft (200).

The well (116) side wall (120) may connect with the well floor (118) via a $2^{nd}$ transition (124) (e.g. FIG. 3A). The $2^{nd}$ transition may have a profile of a circular arc or a straight slope. As guidance, where the rotatable disc (110) has a diameter of 101.6 mm, the $2^{nd}$ transition circular arc radius may be 2-12 mm.

The feed-receiving surface (112) of the flared portion (114) may be curved or straight. Where the flared portion (114) is curved it may be a circular arc. The feed-receiving surface of the flared portion (114) may be smooth.

The flared portion (114) of the feed-receiving surface (112) may be provided with a plurality of radial channels (160, -a, -b). A radial channel (160, -a, -b) is a conduit for molten feed, open at the upwards (20) side, and open at both peripheral (32) and central (30) ends. It is configured to conduct molten feed from the well (116) to the peripheral edge of the flared portion (114). An exemplary rotatable disc (110) provided with radial channels (160, -a, -b) is shown in FIGS. 11 and 12.

The radial channels (160, -a, -b) may be formed as channels protruding above an upward (20) surface of the flared portion (114) as shown, for example, in FIG. 12. The radial channels (160, -a, -b) may be formed as grooves below an upward (20) surface of the flared portion (114).

A radial channel (160, -a, -b) is aligned with line (168) extending radially outwards from the axis of rotation (B-B') of the rotatable disc (110) (see FIG. 11A). The peripheral end of radial channel (160, -a, -b) may meet the peripheral edge (32) of the flared portion (114) of the rotatable disc (110).The central end of the radial channel (160, -a, -b) may or may not meet a central (32) edge of the well (116) of the rotatable disc (110). An annular buffer region (162) of the flared portion (114) extending outwards from the well (116) may be devoid of radial channels (160, -a, -b). The radial channels (160, -a, -b) are preferably confined to the flared portion (114).

A radial channel (160, -a, -b) may have a radial cross-section (170) which is a cross-section (b-b in FIG. 11A) perpendicular to a central radial line (168) of the channel (see FIG. 11B). The radial cross-section (170) may have a rectangular (oblong) form. The longer edge of the oblong may be parallel to the axis of rotation (B-B') of the rotatable disc (110). The size of the cross-section may change from a central (30) to peripheral (32) direction of the radial channel. The size-change may be gradual.

Preferably, the size of the cross-section (170) decreases gradually from a central (30) to peripheral (32) direction of the radial channel. Preferably, the width (Cw) of the cross-section (170) decreases gradually from a central (30) to peripheral (32) direction of the radial channel. The height (Hw) of the cross-section (170) may be constant from a central (30) to peripheral (32) direction of the radial channel. A peripheral annular border (164) of the flared portion (114) may have a reduced cross-section height compared with the cross sections in the remainder of the radial channel. This may be due to a flattening of the top of the channels in the peripheral annular border (164). The radial channels (160, -a, -b) are preferably evenly distributed around the axis of rotation (B-B') of the rotatable disc (110). The radial channel is dimensioned to maintain flow of molten feed within the confines of the channel i.e. without overflowing from the upwards open side. The radial channels providing higher molten feed throughputs while maintaining ideal atomization than could be obtained by the smooth flared disk surface design.

The peripheral rim of the rotatable disc (110) may terminate at an angle of less than 10 deg (e.g. 3-5 deg) above and with respect to a plane perpendicular to the axis of rotation (B-B') of the rotatable disc (110). The flared portion (114) may not or may connect with the well via a $1^{st}$ transition (122) (e.g. FIG. 3A). The $1^{st}$ transition (122) may have a profile of a circular arc.

The feed-receiving surface (112) may be made from any suitable material that maintains its shape integrity under rotation, and has other properties such as durability and corrosion resistance. Examples of suitable materials include stainless steel, high temperature thermoplastic (e.g. Teflon, PEEK), coated materials, such as coated aluminium (anodized, polymer coating, or others), coated steel.

The rotatable disc (110) may be disposed with a heat generator (180) configured to controllably emit heat in order to regulate a temperature of the feed-receiving surface (112). The heat generator may be an inductive heating body (180') configured for heating using wireless inductive heating. An induction coil may be provided above or below the rotatable disc (110) that emits energy in the form of a rapidly alternating magnetic field. The inductive heating body (180') is heated up by eddy currents, induced by the electromagnetic field. The material of the rotatable disc itself may form the inductive heating body (180'), or a separate inductive heating body (180') may be provided attached to the rotatable disc, for instance, on a downward side. An exemplary heat generator (180) as a separate inductive heating body (180') is shown in FIG. 3D. The inductive heating body (180') may comprise any material suitable for inductive heating such as stainless steel, iron or an alloy thereof. The rotatable disc (110) may be disposed with one or more temperature sensors, optionally wireless. The one or more temperature sensors may be disposed on the downward side of the rotatable disc (110), for instance, within a cavity or bore of the heat generator (180) or inductive heating body (180'). The wireless temperature sensors may use Bluetooth (e.g. BLE) or RFID.

The skilled person is able to prepare a rotatable disc (110) according to the requirements of flow rate and particle size. As guidance, the feed-receiving surface of the rotatable disc (110) may have a diameter (Dd) of 101.6 mm and the feed-receiving surface of the well may have a diameter (Wd) of 30 mm. Indicators of dimensions are shown in FIG. 3A. The circular arc radius may be 63.5 mm. The peripheral rim of the rotatable disc (110) may terminate at an angle of less than 10 deg (e.g. 3-5 deg) above and with respect to a plane perpendicular to the axis of rotation (B-B') of the rotatable disc (110). The height of the feed-receiving surface of the well (Wh) (distance between top of well side wall (120) and well floor (118) may be 4-5 mm. The $1^{st}$ transition (122) the circular arc radius may be 8-12 mm, e.g. 10 mm. The $2^{nd}$ transition may have a profile of a circular arc or a straight slope. The $2^{nd}$ transition circular arc radius may be 2-12 mm. The width (Cw) of the radial channel at the peripheral (32) edge of the flared portion (114) may be 200-500 μm (see FIG. 11B). The width (Cw) of the radial channel cross-section (170) at the central (30) end of the disk may be 1-2 μm. The transition from the width (Cw) at the peripheral edge to the central edge may be gradual. The height (Ch) of the radial channel cross-section (170) at the peripheral edge is configured to be sufficiently large in order to prevent the molten feed from flowing up over the walls, preferably equal to or greater than 1 mm. The radial channel cross-section height (Ch) may be constant in a radial direction, The radial channel cross-section height (Ch) may taper-off (i.e. reduce) with the profile of the disk surface in the peripheral annual border (164), for instance, the top surface of the channels may be flattened in the peripheral annual border (164). The number of radial channels (160, -a, -b) may be 50 to 500, for instance 80 to 100. It is appreciated that the dimensions of rotatable disc (110) may be scaled up or down depending on the desired rate of flow of the feed and product.

Hollow drive shaft (200) transmits torque to the rotatable disc (110). Torque is provided to the hollow drive shaft (200) from the motor unit (300), optionally via an outer support shaft (270) (see later below). Hollow drive shaft (200) lumen (202) transports feed in a downwards (22) direction to the apertures (110) for passage across the feed-receiving surface (112) of the rotatable disc (110). Hollow drive shaft (200) lumen (202) is aligned with the axis of rotation (B-B') of the rotatable disc (110) so that the liquid feed is fed centrally into the well (116) of the feed-receiving surface (112).

The hollow drive shaft (200) may be disposed with one or more O-rings to seal the exterior of the hollow drive shaft (200) against the lumen wall of the outer support shaft (270).

The hollow drive shaft (200) may be made from any suitable material that maintains its shape integrity under rotation, and has other properties such as stiffness and durability. Other qualities include compatibility with the liquid feed, for instance, low toxicity and chemical stability. Examples of suitable materials include stainless steel and Teflon-coated materials.

Figure 4A:
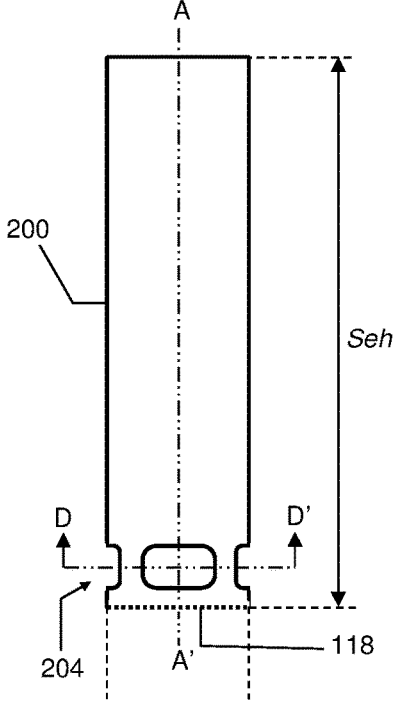
FIGS. 4A to 4D illustrate various views of the hollow drive shaft (FIG. 4A), transverse cross-sectional view across pillars (FIGS. 4B and 4C), side view of aperture (FIG. 4D)
Figure 4B:
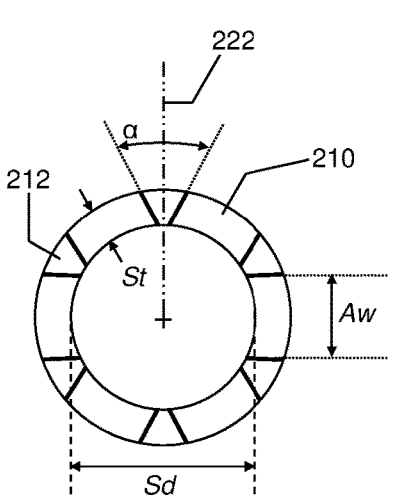

Hollow drive shaft (200) is longitudinal. Hollow drive shaft (200) may have an effective height (Seh) measured from the well floor (118) to the upward (20) terminal end (see FIG. 4A). In general, a reduced effective height (Seh) is preferred to reduce vibrations and instabilities at high rotational speeds. Hollow drive shaft (200) may have a wall thickness (St) (see FIG. 4B). Hollow drive shaft (200) may have a lumen diameter (Sd) (see FIG. 4B). As a non-limiting guidance, the effective height (Seh) may be 200 to 400 mm, wall thickness (St) may be 1 to 5 mm, the lumen diameter (Sd) may be 10 to 25 mm.

The hollow drive shaft (200) comprises a distributor (204) at or towards the downward (22) end configured for the regulation of outward flow of liquid feed. The distributor (204) comprises a plurality of apertures (210) disposed around a circumference of the downward end (22) of the hollow drive shaft (200) for the outflow of the molten feed. A pillar (212, a, b) is disposed between adjacent aperture pairs (210, a, b), the pillar configured to minimally disturb the flow of liquid feed from the well (116) to the flared portion (114) of the feed-receiving surface (112). A pillars (212) may have a longitudinal axis disposed in a direction of the A-A' axis, or at an incline of less than 10 deg.

The distributor (204) may be disposed with a plurality of apertures (210). Exemplary apertures (210) are set out in FIGS. 4A to 4D. The number of apertures (210) in the hollow drive shaft (200) may be 2 to 24, such as for example 3 to 9, preferably 6. The apertures (210) may be evenly disposed around a circumference towards the downward end (22) of the hollow drive shaft (200). Each aperture (210) may have the same shape and dimension. Each aperture (210) may have an aperture height (Ah) in an axial (A-A') direction, and an aperture width (Aw) in a plane perpendicular to the axial (A-A') direction as indicated in FIG. 4D.

Figure 4C:
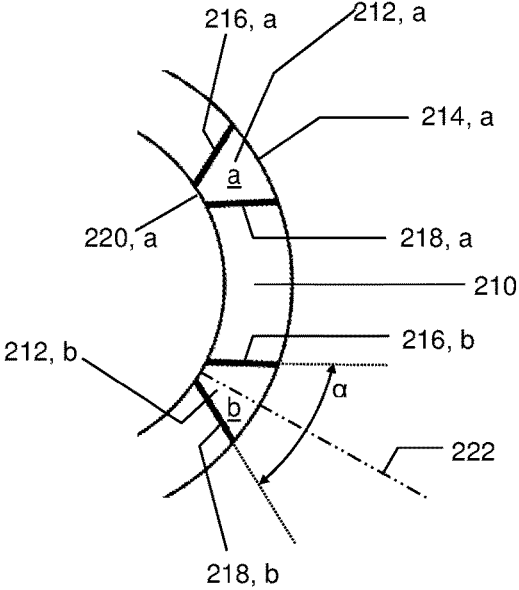
Figure 4D:
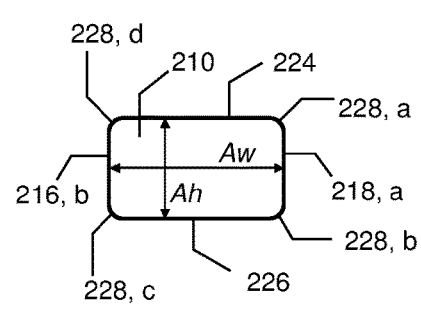

Each aperture (210) may have two opposing parallel straight side edges (e.g. FIG. 4C, 4D 216, b; 218, a). The straight side edges may be parallel to an axial direction (A-A').The side edges (e.g. 216, b; 218, a) are separated by the aperture width (Aw). Each aperture (210) may have opposing upper and lower edges (e.g. 224, 226). The upper and lower edges (e.g. 224, 226) may be parallel to plane perpendicular to the axial direction (A-A'). The upper and lower edges (e.g. 224, 226) may be separated by the aperture height (Ah). The corners (228, a-d) of each aperture (210) may be rounded.

The apertures (210) may be positioned at the same axial position of the hollow drive shaft (200).The apertures (210) may be positioned on the hollow drive shaft (200) at an axial position of hollow drive shaft (200) such that the axial height of the apertures (210) (Ah) is within the axial height of the well (Wh), preferably within the axial span between the top of the well side wall (120) and well floor (118).

The pillar (212, a, b) may have a transverse cross-section. A transverse cross-section of a pillar (212, a, b) is a section across a plane (e.g. FIG. 4A, D-D') perpendicular to the axis of rotation (A-A') of the hollow drive shaft (200). A pillar (212, a, b) transverse cross-section can be seen in FIGS. 4B and 4C. A pillar (212, a, b) transverse cross-section may have a pillar outer edge (214, a), two pillar side edges (216, a, b; 218, a, b) and optionally a pillar inner edge (220, a). The pillar outer edge (214, a) is provided on an outer surface of the hollow drive shaft (200); it is typically rounded (convex) to correspond with the rounded outer surface of the hollow drive shaft (200). The pillar side edges (216, a, b; 218, a, b) are formed by the thickness of the hollow drive shaft (200) wall; they are typically straight. The pillar inner edge (220, a) is provided on an inner surface of the hollow drive shaft (200); it may be rounded (concave) to correspond with the rounded inner surface of the hollow drive shaft (200).

A pillar (212) in transverse cross section may have a plane of symmetry (222) that is parallel to and crosses the axis of rotation (A-A') of the hollow drive shaft (200).

The side edges (e.g. 216, b and 218 b) of the same pillar (e.g. 212, b) may converge in a direction towards the centre (30) of the hollow drive shaft (200). In other words, axes parallel to and touching the pillar side edges (e.g. 216, b and 218 b) cross towards the centre (30) (not periphery 32) of the hollow drive shaft (200). They cross at an angle alpha (α). The side edges (e.g. 216, b and 218 b) of the same pillar (e.g. 212, b) may be mutually disposed at an angle alpha (α) formed towards the centre (30) of the hollow drive shaft (200). Angle alpha (α) may be less than 180 deg, preferably 10 to 80 deg. When there are 6 apertures, alpha is preferably 60 deg. Side edge of mutually adjacent pillars (e.g. 218, a and 216, b) i.e. side edges of pillars forming an aperture (210) may be mutually parallel (see FIG. 4C).

The inventors have found that when side edges (e.g. 216, b and 218 b) of the same pillar (e.g. 212, b) converge in a direction towards the centre (30) (not periphery 32) of the hollow drive shaft (200) there are less starved regions of the feed-receiving surface compared with other configurations. FIG. 5A shows a flow across a feed-receiving surface wherein the side edges of the same symmetrical pillar converge in a direction towards the centre of the hollow drive shaft (FIG. 5A'); starved areas (94) are narrow and faint. FIG. 5B shows a flow across a feed-receiving surface wherein side edges of the same pillar converge in a direction towards the periphery of the hollow drive shaft (FIG. 5B'); starved areas (94) are more frequent and pronounced. FIG. 5C shows a flow across a feed-receiving surface wherein the pillars are non-symmetrical (FIG. 5C'); starved areas (94) are highly pronounced.

The geometries of the pillars, well, and centrally aligned feed combine produce a uniform film of liquid feed on the disc surface which leads to a well-defined and narrow atomization profile and robust particle size control. In particular, for high throughput with some molten feeds, it can be problematic to obtain the desired particle size and size distribution. The top drive that aligns the disc with delivery of the molten feed to the disk, the distributor and rotatable disc shape improve homogeneity of the molten feed across the spinning disk. The use of radial grooves on the feed receiving surface of the disc maintains ideal atomization by inducing ligament formation (rather than sheeting) at higher throughputs. At a higher flow rate a standard disk may exhibit sheet formation (inferior atomization), while the channeled disk exhibit a ligament regime (superior atomization).

The hollow drive shaft (200) may be dismountably attachable at its downward (22) end to the rotatable disc (110). The hollow drive shaft (200) may pass through an opening (130) in well base end (117) of the rotatable disc (110) and attach to the rotatable disc (110) using one or more fittings. The hollow drive shaft (200) may be provided with one or more sealing elements (206) (e.g. O-rings) to seal an exterior of the hollow drive shaft (200) to the feed-receiving surface of the well (216). The hollow drive shaft (200) may be attached to the rotatable disc (110) using any means, including one or more fixtures (e.g. bolts). The hollow drive shaft (200) may be attached to the rotatable disc (110) using a shaft plug (250) that clamps the parts together via a bayonet fitting or a flanged end of the hollow drive shaft (200).

Figure 7A:
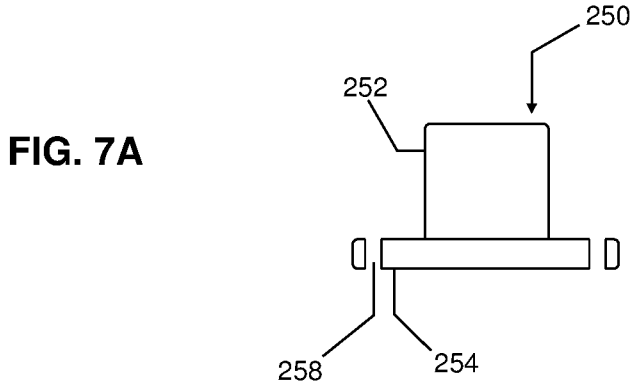
FIGS. 7A to 7C are schematic illustrations of shaft plug.
Figure 7B:
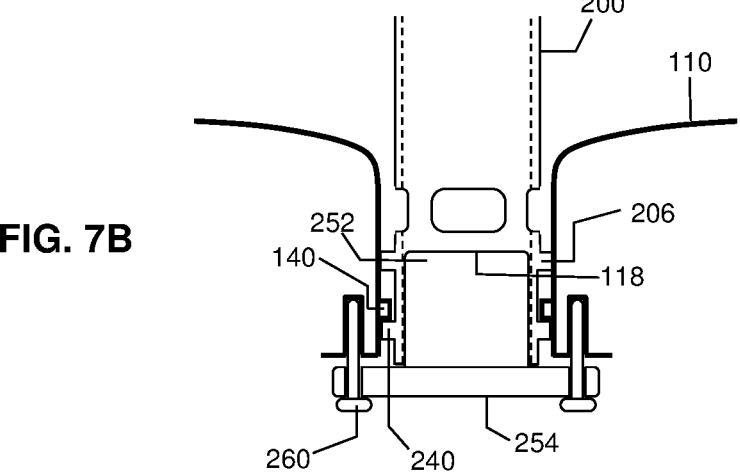
Figure 7C:
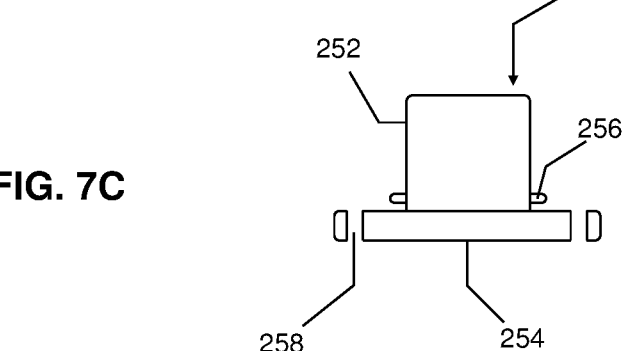

A shaft plug (250) may be provided having a plug head (254), and a plug body (252) attached to the plug head (254). Exemplary shaft plugs are shown in FIGS. 7A to C, and FIG. 6D. The plug body (252) is insertable in an upwards (22)

direction into and sealingly fitting into the lumen (202) of the hollow drive shaft (200) at the downward end (22) of the hollow drive shaft (200). The plug body (252) may be disposed with one or more O-rings (258) to seal the plug body (252) against the wall of the hollow drive shaft (200). A top surface of the plug body (252) may form the well floor (118). In FIG. 7A, the plug body (252) is devoid of plug key; it may be employed where the hollow drive shaft (200) and the rotatable disc (110) are devoid of a bayonet fitting described later below. In FIGS. 7B and 7C a plug key (256) is provided in order to rotate the aforementioned bayonet fitting where present.

The plug head (254) is attachable to the rotatable disc (110) from the downwards side (22). The plug head (254) may be disposed with one or more passages (258) to allow attachment to the rotatable disc (110) using one of more fixtures (260) such as a retaining bolt. Tightening of the plug head (254) to the rotatable disc (110) by the fixtures (260) clamps the plug body (252) into position and seals the well (116).

Where the bayonet fitting described later below is present, the plug head (254) also provides a grip for rotation of the plug key (254), and clamps the bayonet fitting (140, 240) together.

Where the hollow drive shaft (200) has flanged end, the plug head (254) clamps the flanged part against an annular ring disposed between an upwards (20) end of the flange and a downwards (22) end of the rotatable disc (110), thereby attaching the hollow drive shaft (200) to the rotatable disc (110).

Figures 6A, 6B, 6C, 6D:
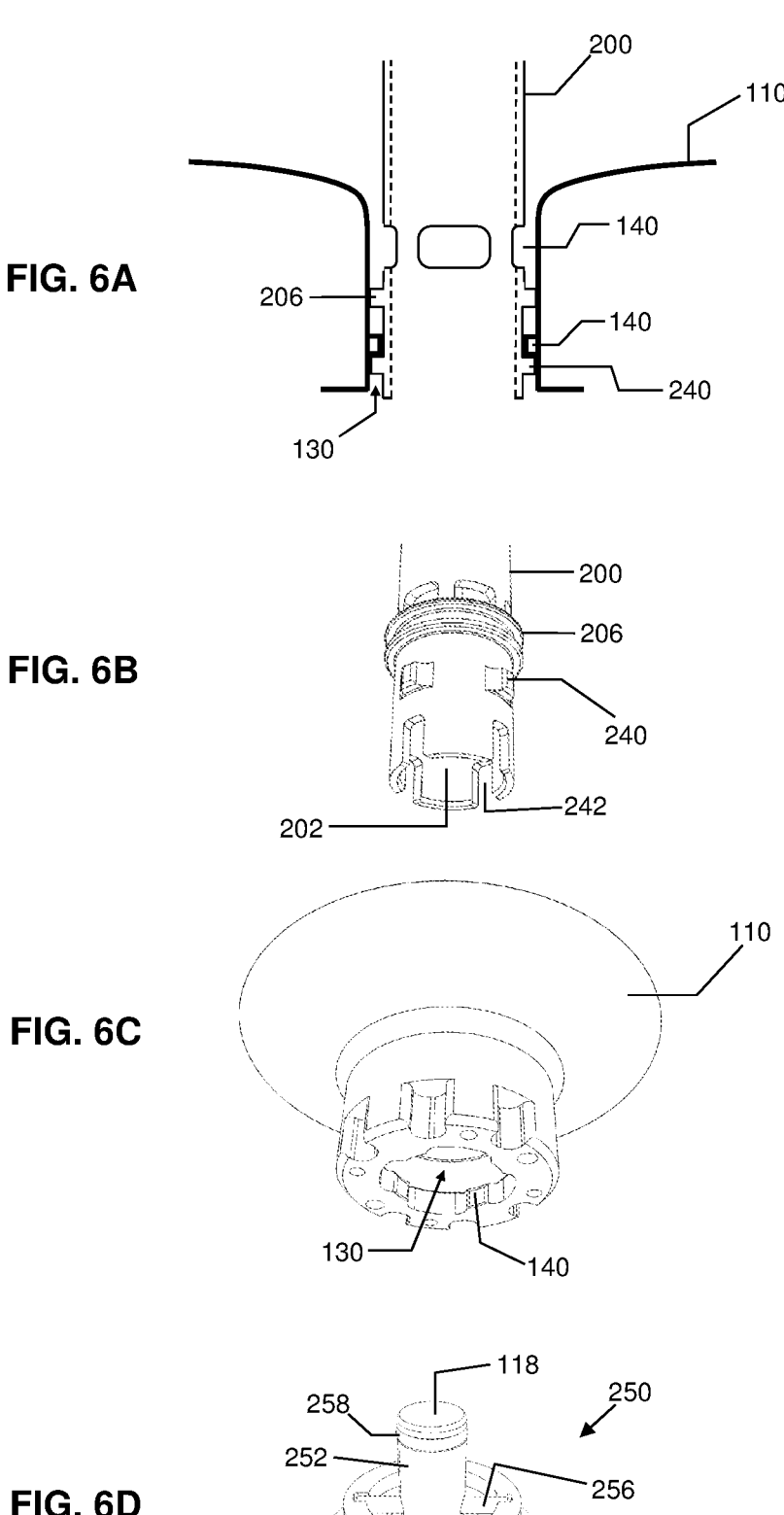
FIGS. 6A to 6D are schematic illustrations of bayonet fitting, and shaft plug.

A bayonet fitting (140, 240) may be provided on the downward end (22) of the hollow drive shaft (200) and the rotatable disc (110), in particular in the well (116). An exemplary bayonet fitting is shown in FIGS. 6A to 6C. The bayonet fitting may comprise a set of spaced-apart protrusions (240) provided on an exterior of the hollow drive shaft (200), and a complementary set of the spaced-apart protrusions (140) provided on an interior of the of the well (116) towards the base end (117). The respective spaced-apart protrusions (140, 240) are able slide past each other when they are aligned with gaps between the protrusions (140, 240) in the corresponding part. The respective spaced-apart protrusions (140, 240) engage and prevent sliding apart when they are aligned together. In other words, the bayonet fitting in a position allows downward (22) insertion of the hollow drive shaft (200) through the opening (130) in the rotatable disc (110), and in a $2^{nd}$ position prevents removal of the hollow drive shaft (200) through the opening (130) in the rotatable disc (110) in an upwards (20) direction. Movement between the $1^{st}$ and $2^{nd}$ position is by an axial (A-A') rotation of the hollow drive shaft (200).

A plug key (256) disposed in fixed relation to the plug head (254) may be provided on the plug body (252) attached to the plug head. The plug key may comprise one or more protrusions (e.g. radial protrusions) from the plug body (252). The plug key (254) engages with one or more slots (242) on the hollow drive shaft (200). The one or more slots may be provided on a downward (22) edge of the hollow drive shaft (200). Engagement of the plug key (254) with the one or more slots allows the hollow drive shaft (200) to be turned relative to the rotatable disc (110) while positioned in the well (116) opening (130). The plug key (254) allows engagement and disengagement of the bayonet fitting.

It is appreciated that the bayonet fitting may be absent from the downward end (22) of the hollow drive shaft (200) and the rotatable disc (110); in which case the plug key is not needed on the plug body (252).

The shaft plug (250) may be made from any suitable material that maintains its shape integrity under rotation, and has other properties such as durability and corrosion resistance. Other qualities include compatibility with the liquid feed, for instance, low toxicity and chemical stability. Examples of suitable materials include stainless steel and Teflon-coated materials.

Figures 9A, 9B, 9C, 9D, 9E:
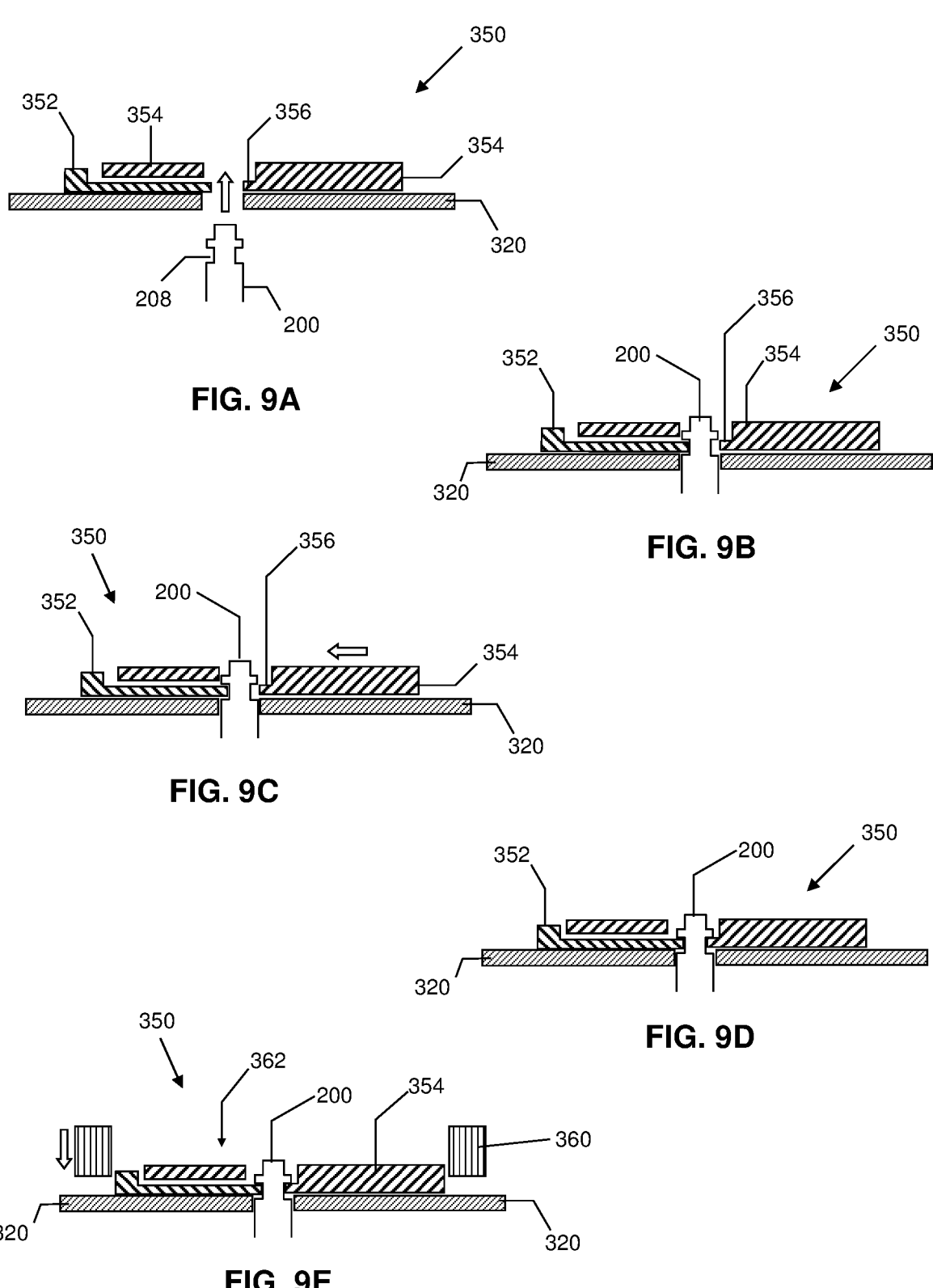
FIGS. 9A to 9E are schematic illustrations of a hub element mounting block.

The hollow drive shaft (200) may be dismountably attachable at the upward (20) end to a releasable mounting (350). An exemplary releaseable mounting is shown in FIGS. 9A to 9E. The hollow drive shaft (200) at the upward end may comprise an annular groove (208). The annular groove (208) engages with the releasable mounting (350). The releasable mounting (350) may comprise spring latch (352) and a push slider (354), wherein the annular groove engages with the spring latch (352) thereby maintaining a fixed axial position of the hollow drive shaft (200). In FIG. 9B, the spring latch (352) is first engaged with the annular groove (208). The push slider (354) may be configured to slide perpendicular to the axis of rotation (A-A') of the hollow drive shaft and has a deployed and release position. The push slider (354) may be disposed with a protrusion (356) configured to engage with the annular groove (208) in the deployed position. In FIG. 9B, push slider (354) is in the release position. In FIG. 9C, push slider (354) is being moved to the deployed position. In FIG. 9D, push slider (354) is in the deployed position. The annular groove (208) may at one circumferential part engage with the spring latch (352) and at another circumferential part with the push slider (354). The releasable mounting (350) allows for a fast and secure releasable attachment of the hollow drive shaft (200) to the chassis assembly (320).

The push slider (354) may be lockable in a deployed position by one or more fasteners (e.g. screw fastener). The one or more screw fastener may additionally raise the push slider (354) and spring latch (352) in an upwards direction, where push slider (354) and spring latch (352) engage with a distance limiter; friction between the distance limiter and the push slider (354)/spring latch (352) ensures that the latter maintain a fixed position.

The push slider (354) may be guarded in the deployed position by a hub element mounting block (360) (see FIG. 9E). The hub element mounting block (360) may contain collar-like body that defines a receiving space (362). The push slider (354) in the deployed position and the spring latch (352) in the biased (latched on to the hollow drive shaft (200) annular groove) may be fittingly engage in the receiving space (362) of the hub element mounting block (360), thereby preventing the push slider (354) from moving to the release position while the hub element mounting block (360) is in position. The hub element mounting block (360) may be attachable to the chassis assembly (320). The releasable mounting (350) may rotate relative to the chassis assembly (320). The releasable mounting (350) may be provided in fixed (axial) rotation relation to the outer support shaft (270) (described below).

The hub element mounting block (360) element mounting block (320) may be utilised as a dismountable safety lock to prevent the push slider (356) from moving to a release position during operation. In a situation where the fastener would loosen, friction between the distance limiter and the push slider (354) would be released and centrifugal forces generated by the rotating hollow drive shaft (200) would cause it to displace radially and to push slider (354) outwards. The hub element mounting block (360) would prevent the push slider (354) from fully releasing the hollow drive shaft (200) by acting as a stop member. Repeated collision between the hub element mounting block (360) and the push slider (354) would generate an audible alert, alarming the operator to safely stop rotation induced by the motor unit (300). The hub element mounting block (360) hence prevents the damage caused by release of the hollow drive shaft (200) and rotatable disc (110) at high speed.

Figure 8A:
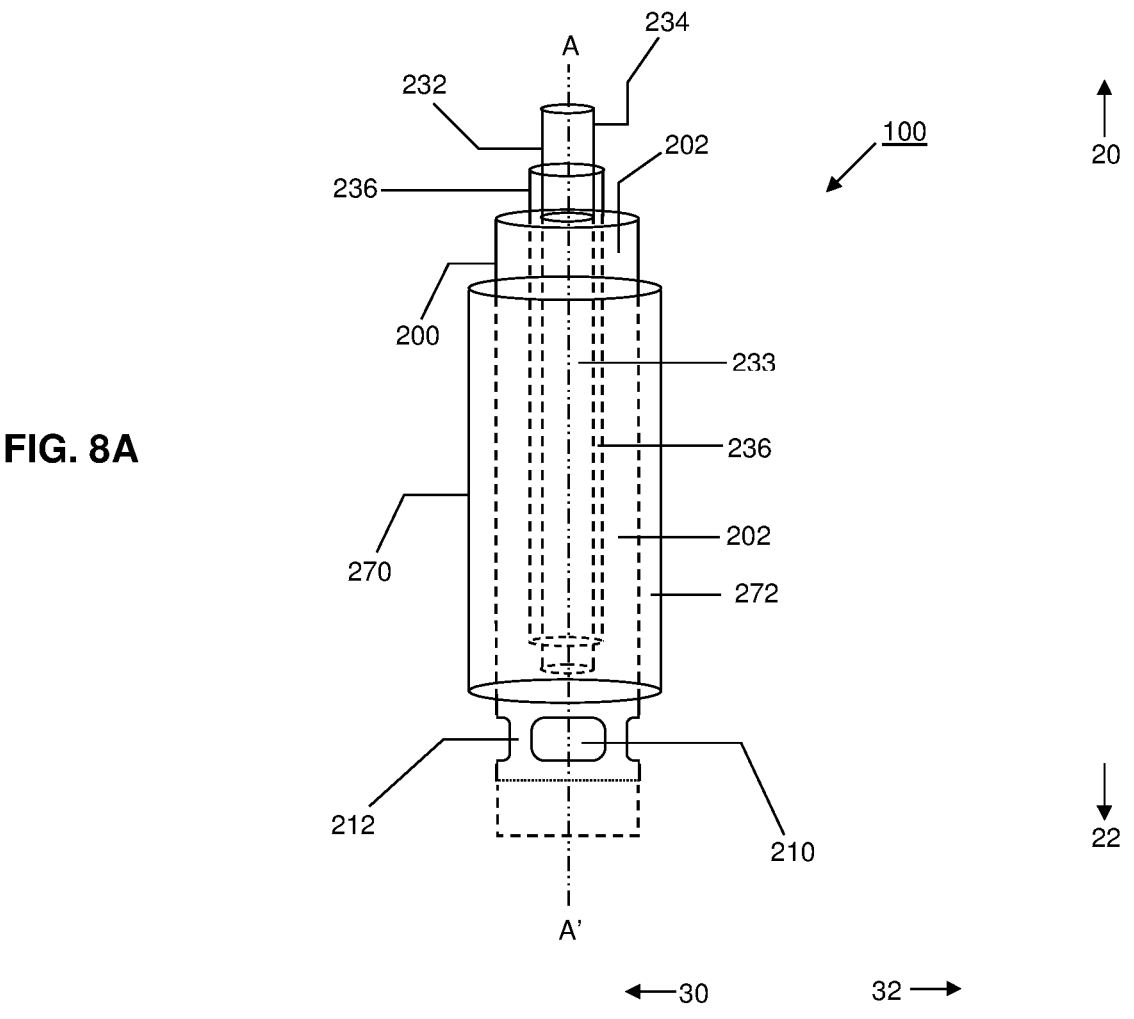
FIGS. 8A and 8B are schematic illustrations of arrangement of shafts and tubes.
Figure 8B:
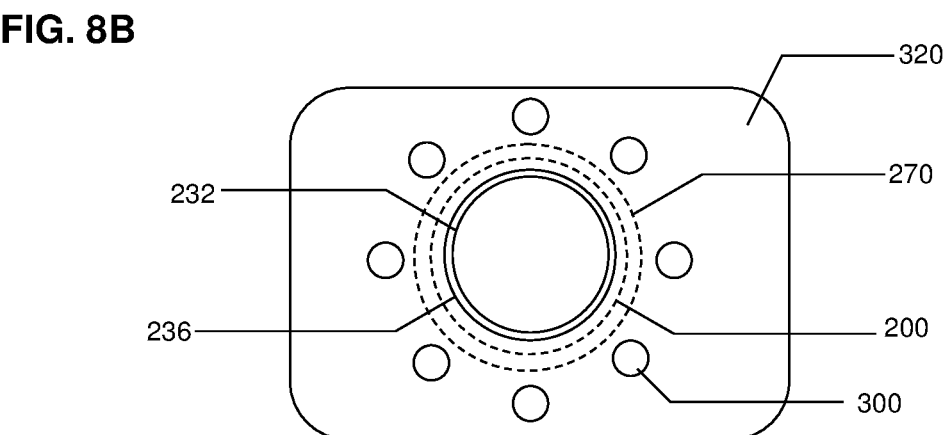

The spinning disc sprayer (100) may further comprise a hollow outer support shaft (270) having a longitudinal shaft lumen (272) for receiving the hollow drive shaft (200). An exemplary outer support shaft (270) is shown in FIGS. 8A and 8B. The outer support shaft (270) may be non-dismountably (except for service) connected to the torque output of the motor unit (300). The lumen (272) of the outer support shaft (270) may be configured to fittingly receive the drive shaft (200). The outer support shaft (270) may be supported on one or more bearings (e.g. roller bearings) by a part of a chassis assembly (320) (supporting stationary part).

A chassis assembly (320) is a static part of the spinning disc sprayer (100) which supports one or more parts of the spinning disc sprayer (100). The chassis assembly (320) may be a single piece, or maybe made up of one or more pieces rigidly and permanently (for a duration of the service life) mutually attached.

The outer support shaft (270) rotates along an axis of rotation (A-A') of the hollow drive shaft (200). Axial (A-A') rotation of the outer support shaft (270) by torque output of the motor unit (300) causes rotation of the hollow drive shaft (200). Torque is transmitted from the outer support shaft (270) to the hollow drive shaft (200) by frictional forces. The outer support shaft (270) may be disposed in fixed (axial) rotational relation to the releasable mounting (350); path of torque may follow in sequence motor unit (300)—outer support shaft (270)—releasable mounting (350)—hollow drive shaft (202).

The outer support shaft (270) may be made from any suitable material that maintains its shape integrity under rotation, and has other properties such as stiffness and durability. Examples of suitable materials include brass, stainless steel, aluminum (coated or uncoated), steel (coated or uncoated), polymeric material.

The spinning disc sprayer (100) may further comprise a static (non-rotating) rigid product feed tube (232) that extends within the lumen (202) of the drive shaft (200) downwards (22) towards the apertures (210). An exemplary rigid product feed tube (232) is shown in FIGS. 8A and 8B. The rigid product feed tube (232) has an axial lumen (233) for the passage of feed to the apertures (232). The rigid product feed tube (232) may not axially (A-A') extend into the axial region occupied by the distributor (204) or apertures (210). The rigid product feed tube (232) may terminate upwards of the distributor (204) or apertures (210), for instance, by a distance of greater than 1 to 25 mm. The product feed tube unit (230) may be dimensioned such that there is a clearance between the drive shaft (200) and an outer surface of the product feed tube (232). The product feed tube unit (230) has a feed inlet (234). The feed inlet (234) conveys feed to the rigid product feed tube (232).

A hub element may be provided for attachment of the product feed tube (230) to the chassis assembly (320) e.g. by one or more retaining bolts. The rigid product feed tube (232) may be rigidly attached at its upward (20) end to the hub element. The hub element may be dismountably attached to the chassis assembly (320), optionally via the hub element mounting block (360). The feed inlet (234) of the product feed tube (230) may be integrated into or be supported by the hub element.

The outer support shaft (270) may be made from any suitable material having requisite properties of stiffness, durability and thermal conductivity. Examples of suitable materials include stainless steel.

The spinning disc sprayer (100) may further comprise a heating element tube (236) for heating at least a part of the rigid product feed tube (232). An exemplary rigid product feed tube (232) is shown in FIGS. 8A and 8B. The heating element tube comprises (236) an electrical heating element having a tube-like form with a lumen into which the rigid product feed tube (232) fits. The heating element tube (236) may be flexible. Electrical cable supplying power to the heating element tube (236) may exit via the hub element. The heating element tube comprises (236) may extend over 90% of the axial length of the rigid product feed tube (232). The heating element tube (236) may be attached at the upwards end (20) to the hub element.

The spinning disc sprayer (100) may be further provided with an optical camera, configured to capture during spraying one or more images of at least a part of the feed-receiving surface and feed particles being sprayed from the feed-receiving surface. The optical camera may be configured to capture a periphery part (32) of the feed-receiving surface. The optical camera may be linked to a trigger, configured to trigger capture of an image according to an angular rotational position of the rotatable disc.

Figure 10:
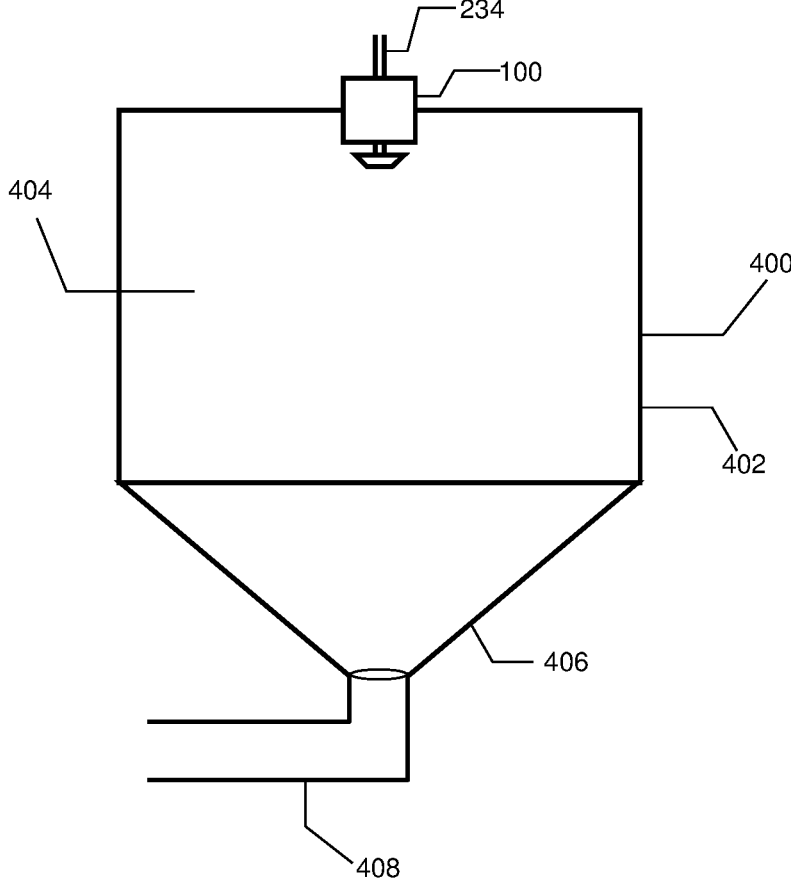
FIG. 10 is a schematic illustration of spinning disc sprayer (100) disposed within process container.

The spinning disc sprayer (100) may be disposed attached to a process container (400). In particular, it may be attached to an upwards end (top) of the process container. An exemplary process container (400) is shown in FIG. 10. The process container has a containing wall (402) enclosing a container volume (404) in which particles ejected from the rotatable disc (110) can undergo transformation (e.g. congeal) and fall towards the base (406) where they are collected. An outlet (408) of the container (400) removes the formed product. The spinning disc sprayer (100) may be configured for partial insertion into the process container (400), wherein the rotatable disc (110) is immersed in the container volume (404) and the upward end (20) of the spinning disc sprayer (100) is outside the container (400) or container volume (404). Provided may be a system comprising a spinning disc sprayer (100) and a process container.

FIGS. 13A-17B illustrate another embodiment of the spinning disc sprayer (100) that includes an alternative connection system between the hollow shaft (200) and disc (110). Except as otherwise described below, the structure and operation of spinning disc sprayer in this embodiment can be the same as described in other embodiments. For example, the geometry of fluid path, upper disc surface, pillars and windows can be the same as that of the other embodiments described herein.

Figure 13A:
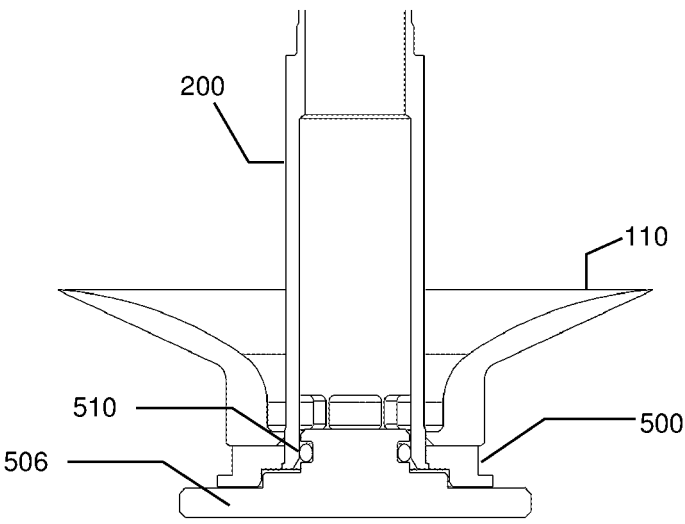
FIGS. 13A to 13B are cross-sectional views of a rotatable disc coupled to a flange of a hollow drive member.
Figure 13B:
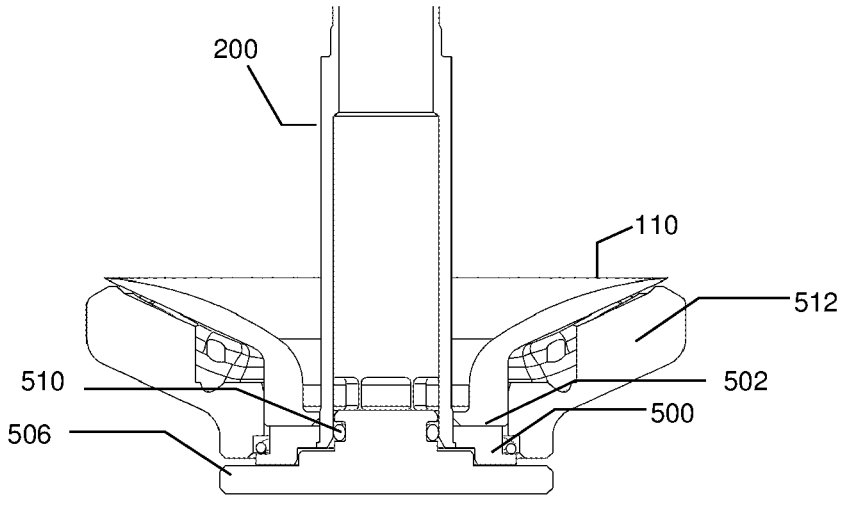

FIGS. 13A-13B show cross-sectional views of hollow drive shaft (200) having a flange (500) secured to the hollow drive shaft (200) at a lower end portion of the hollow drive shaft. Flange (500) can be secured to the hollow drive shaft (200) in any suitable manner. Preferably, the flange is welded to the bottom of the hollow drive shaft; however, it should be understood that the flange can be integrally formed with the hollow drive shaft (e.g., machined from a single part) or coupled to the shaft by any other suitable fasteners.

As shown in FIGS. 13A-13B, disc 110 can be received on an upper surface (502) of flange (500). In some embodiments, the upper surface (502) can be flat to engage with a correspondingly shaped lower surface of the disc (110). Alternatively, other shapes for the upper surface of the flange and lower surface of the disc can be provided, so long as the surfaces can correspondingly engage with one another to permit the connection described herein.

To secure the disc (110) to the hollow drive shaft (200), an opening (504) in the disc (100) (FIG. 16B) can be placed over the hollow drive shaft (200), and the disc (110) can be dropped down from the top of the shaft until the lower surface of the disc rests on the upper surface (502) of the flange (500). Then a shaft plug (506) can be positioned below a bottom surface (508) of the flange (500) and the shaft plug can be secured to the flange and the disc (110).

As shown in FIGS. 13A-13B, the shaft plug (506) is positioned below the flange and the disc is positioned above the flange. In some embodiments, there is no need to provide an additional sealing member (e.g., an O-ring) between the shaft and disc because the connection (as described in more detail below) between the upper surface of the flange and the lower surface of the disc provides sufficient sealing. As shown in FIGS. 13A and 17B, for example, a sealing member (510), e.g., an O-ring, can be provided to achieve a tighter seal between the plug and an inner surface of the shaft. FIG. 13B also illustrates a cover 512 that can include one or more sensors (e.g., temperature sensors) as described above.

Figure 14A:
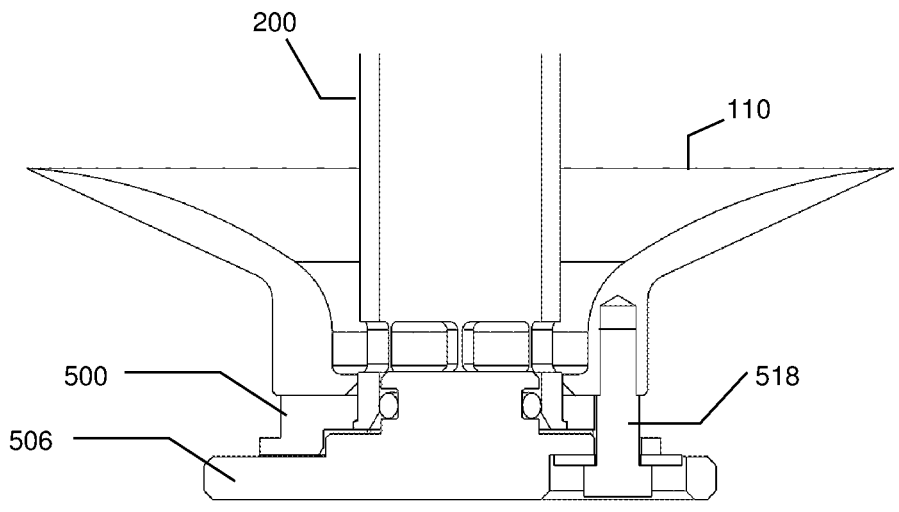
FIGS. 14A to 14B are additional cross-sectional views of a rotatable disc coupled to a flange of a hollow drive member.
Figure 14B:
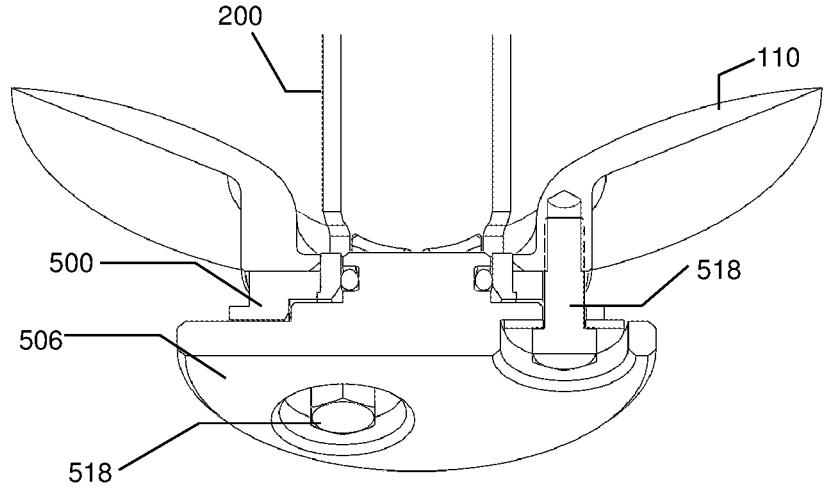

FIGS. 14A-14B are cross-sectional views that show an exemplary fastener system for securing the shaft plug (506) to the flange (500) and disc (110). Shaft plug (506) can have one or more first openings (512) that correspond to second openings (514) in the flange and third openings (516) in the disc (110). One or more fasteners (518) can extend through the respective corresponding openings and secure them together as shown in FIGS. 14A-14B. For example, fasteners (518) can be screws that extend through first openings (512), second openings (514), and third openings (516), and engage with threaded portions of the third openings (516) and, optionally, one or more of the first and second openings.

Figure 17A:
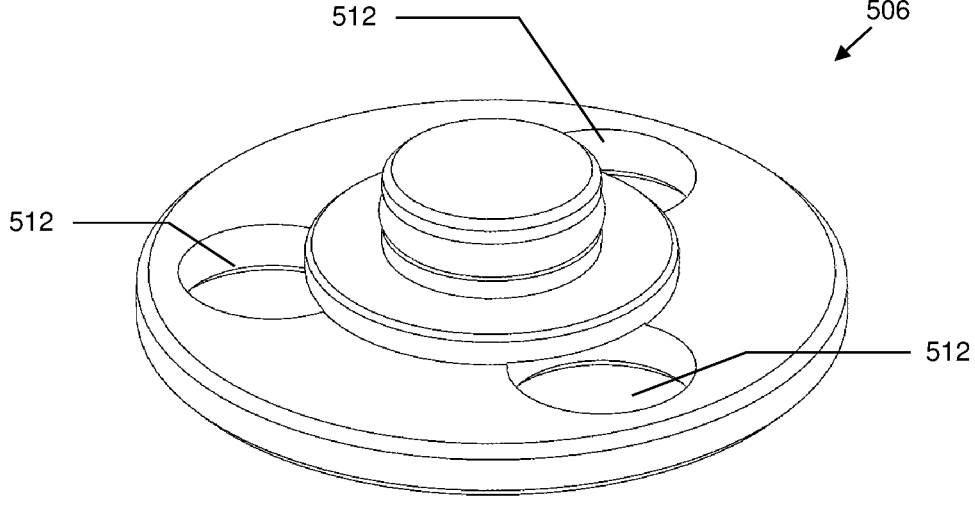
FIGS. 17A to 17B are views of a shaft plug configured to be attached to a flange of a hollow drive shaft.
Figure 17B:
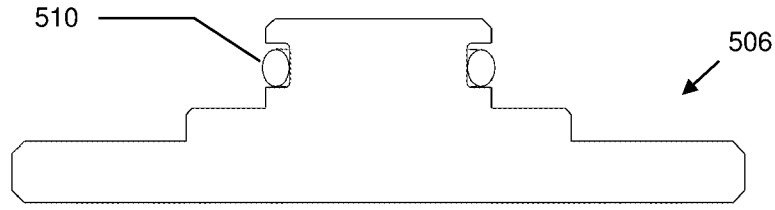

FIG. 17A shows a plurality of first openings (512) in shaft plug (506). In some embodiments, the number of corresponding openings in each structure can vary and can be one or more. Preferably, the number of openings provided in each structure are between one and four, and preferably include at least two or at least three openings.

FIGS. 15A-15C show a plurality of second openings (514) in the flange (500). As discussed above, the number of second openings can vary, but are shown in the figures with three second openings. As can be seen in FIGS. 15A-15C, and as described in other embodiments, a plurality of apertures (210) can be disposed around a circumference of the downward end of the hollow drive shaft (200) for the outflow of the molten feed. Flange (500) is located below the plurality of apertures (210).

FIGS. 16A-16O show a plurality of third openings (516) in the disc (110). Three third openings are shown in these figures which corresponds to the number of first and second openings in FIGS. 15A-15C and FIG. 17A. The third openings can have internal threads that engage with a fastener (e.g., a screw) to secure the shaft plug (506) to the flange (500) and third openings (516) of disc (110).

The alternative connection system shown in FIGS. 13A-17B can provide several advantages over other system. While maintaining the desirable functions of the spinning disc sprayers described herein that use other connection methods, this connection method can provide improved safety of operation since the disc cannot fall off the flange even if the fasteners fail. In addition, in some embodiments, the alternative connection system can allow for lighter and shorter connection components, which can reduce potential undesirable off-axis vibrations at higher rotation speeds.

Provided herein is a use of a spinning disc sprayer (100) as described herein for a melt-spray-congeal (MSC) process. Provided herein is a use of a spinning disc sprayer (100) as described herein for a producing multiparticulates from a molten feed.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of making multiparticulates, comprising:
providing a molten feed comprising an active ingredient and an excipient;
providing a spinning disc sprayer comprising:
a rotatable disc having a feed-receiving surface and an axis of rotation, the feed-receiving surface defining a well centered on the axis of rotation; and
a hollow drive shaft having a longitudinal shaft lumen and an axis of rotation attached to the rotatable disc;
directing the molten feed through the lumen onto the feed-receiving surface, and atomizing the molten feed from the rotatable disc to form solid multiparticulates;
wherein the axes of rotation of the hollow drive shaft and rotatable disc are coaxial, a downward end of the hollow drive shaft is disposed with a distributor for regulating flow of the molten feed into the well, and the distributor and the well are together configured for providing a substantially radial, uniform outward flow of the molten feed across the feed-receiving surface,
wherein the number of rotatable discs is one and the number of feed-receiving surfaces is one, and
wherein the distributor comprises a plurality of apertures disposed around a circumference of the downward end of the hollow drive shaft for an outflow of the molten feed.

2. The method according to claim 1, wherein the feed-receiving surface comprises a peripheral flared portion that slopes gradually in a central and downwards direction towards the well, the well extending further downwards towards a well base end, wherein at least a portion of the feed-receiving surface of the well is more steep than at least a portion of the feed-receiving surface of the flared portion.

3. The method according to claim 2, wherein the flared portion of the feed-receiving surface is provided with a plurality of radial channels, wherein each channel is a conduit for molten feed, open at an upwards side, and open at both peripheral and central ends and configured to conduct molten feed from the well to a peripheral edge of the flared portion.

4. The method according to claim 1, wherein the rotatable disc is disposed on a downward side with a heat generator configured to regulate a temperature of the feed-receiving surface.

5. The method according to claim 1, wherein a pillar is disposed between adjacent aperture pairs, the pillar having in transverse cross section a pillar outer edge, two pillar side edges and optionally a pillar inner edge, wherein the side edges of the pillar converge in a direction towards the center of the hollow drive shaft.

6. The method according to claim 2, wherein the hollow drive shaft is dismountably attachable at its downward end through an opening in the well base end of the rotatable disc.

7. The method according to claim 1, wherein the hollow drive shaft has a flange at its downward end, wherein an upper surface of the flange is configured to receive a lower surface of the rotatable disc.

8. The method according to claim 7, wherein a shaft plug engages with a lower surface of the flange and the rotatable disc is secured to the flange by a plurality of fasteners that extend through a plurality of first openings in the shaft plug, a plurality of second openings in the flange, and a plurality of third openings in the rotatable disc.

9. The method according to claim 1, wherein the hollow drive shaft is dismountably attachable at an upward end to a releasable mounting.

10. The method according to claim 1, wherein the spinning disc sprayer is further provided with a hollow outer support shaft having a longitudinal shaft lumen for receiving the drive shaft.

11. The spinning disc sprayer to claim 1, further provided with an optical camera, configured to capture during spraying one or more images of at least a part of the feed-receiving surface, and feed-particles being sprayed from the feed-receiving surface.

12. The method to claim 1, wherein the spinning disc sprayer is configured for partial insertion into a process container having a container volume in which particles ejected from the rotatable disc can undergo transformation, wherein the rotatable disc is immersed in the container volume and an upward end of the spinning disc sprayer is outside the container.

13. The method according to claim 1, wherein the molten feed comprises at least one active agent and at least one excipient.

14. The method according to claim 13, wherein the at least one excipient is an alkyl-containing glycerol.

15. The method according to claim 13, wherein the at least one excipient is a mixture containing mono-, di- and triglyceryl behenates, glyceryl tristearate, hydrogenated cottonseed oil, hydrogenated castor oil, stearyl alcohol, stearic acid and palmitic acid 50, carnauba wax, candelilla wax, stearoyl polyoxylglyceride, or polyglycerol esters of fatty acids.

16. The method according to claim 1, wherein the molten feed further comprises at least one of a pore former, a swelling agent, a modified release material, and a viscosity modifier.

17. The method according to claim 1, wherein the multiparticulates have a particle size range of from 100 μm and up to about 3 mm.

* * * * *